United States Patent
Ecsedy et al.

(10) Patent No.: US 10,213,436 B2
(45) Date of Patent: Feb. 26, 2019

(54) METHODS OF TREATING CANCER USING AURORA KINASE INHIBITORS

(71) Applicant: Millennium Pharmaceuticals, Inc., Cambridge, MA (US)

(72) Inventors: Jeffrey A. Ecsedy, Newton, MA (US); Wen Chyi Shyu, Cambridge, MA (US); Arijit Chakravarty, Lexington, MA (US); Robert W. Kleinfield, Upton, MA (US); Kha N. Le, Danville, CA (US); Karthik Venkatakrishnan, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/844,270

(22) Filed: Sep. 3, 2015

(65) Prior Publication Data

US 2016/0193224 A1   Jul. 7, 2016

Related U.S. Application Data

(63) Continuation of application No. 13/804,570, filed on Mar. 14, 2013, now abandoned.

(60) Provisional application No. 61/613,258, filed on Mar. 20, 2012.

(51) Int. Cl.
*A61K 31/55* (2006.01)
*A61K 31/337* (2006.01)
*A61K 31/551* (2006.01)

(52) U.S. Cl.
CPC ............ *A61K 31/55* (2013.01); *A61K 31/337* (2013.01); *A61K 31/551* (2013.01)

(58) Field of Classification Search
CPC ..... A61K 31/55; A61K 31/337; A61K 31/551
USPC ........................................................ 514/210
See application file for complete search history.

(56) References Cited

U.S. PATENT DOCUMENTS

| | | | |
|---|---|---|---|
| 4,099,012 A | 7/1978 | Gschwend | |
| 4,469,633 A | 9/1984 | Trybulski | |
| 4,481,142 A | 11/1984 | Fryer et al. | |
| 5,166,151 A | 11/1992 | Freidinger et al. | |
| 5,210,082 A | 5/1993 | Bock et al. | |
| 5,747,487 A | 5/1998 | Albright et al. | |
| 6,057,329 A | 5/2000 | Davis et al. | |
| 6,277,844 B1 | 8/2001 | Spector et al. | |
| 6,727,251 B2 | 4/2004 | Bebbington et al. | |
| 7,572,784 B2 | 8/2009 | Claiborne et al. | |
| 8,026,246 B2 | 9/2011 | Claiborne et al. | |
| 8,399,659 B2 | 3/2013 | Claiborne et al. | |
| 9,102,678 B2 | 8/2015 | Claiborne et al. | |
| 9,765,076 B2 | 9/2017 | Claiborne et al. | |
| 9,765,078 B2 | 9/2017 | Claiborne et al. | |
| 9,988,384 B2 | 6/2018 | Claiborne et al. | |
| 2003/0022885 A1 | 1/2003 | Bebbington et al. | |
| 2003/0055068 A1 | 3/2003 | Bebbington et al. | |
| 2005/0156102 A1 | 7/2005 | Hagleitner et al. | |
| 2005/0256102 A1 | 11/2005 | Claiborne et al. | |
| 2006/0074074 A1 | 4/2006 | Ohtsuka et al. | |
| 2007/0185087 A1 | 8/2007 | Claiborne et al. | |
| 2007/0238716 A1 | 10/2007 | Murthy et al. | |
| 2008/0167292 A1 | 7/2008 | Claiborne et al. | |
| 2009/0299060 A1 | 12/2009 | Claiborne et al. | |
| 2010/0310651 A1 | 12/2010 | Mittal | |
| 2011/0312942 A1 | 12/2011 | Claiborne et al. | |
| 2011/0312943 A1 | 12/2011 | Claiborne et al. | |
| 2014/0046055 A1 | 2/2014 | Claiborne et al. | |
| 2015/0166545 A1 | 6/2015 | Claiborne et al. | |
| 2016/0185782 A1 | 6/2016 | Claiborne et al. | |

FOREIGN PATENT DOCUMENTS

| | | |
|---|---|---|
| CN | 1486310 A | 3/2004 |
| CN | 101547924 A | 9/2009 |
| EP | 0014470 A2 | 8/1980 |
| EP | 0273697 A2 | 7/1988 |
| EP | 2497772 A1 | 9/2012 |
| JP | 2001-507349 A | 6/2001 |
| JP | 2004-533999 A | 11/2004 |
| JP | 2007-522217 A | 8/2007 |
| JP | 2007-537268 A | 12/2007 |
| JP | 4467616 B2 | 5/2010 |
| JP | 5148358 B2 | 2/2013 |
| TW | 200829589 A | 7/2008 |
| WO | WO-97/19065 A1 | 5/1997 |
| WO | WO-97/32883 A1 | 9/1997 |
| WO | WO-98/28281 A1 | 7/1998 |
| WO | WO-98/058926 A1 | 12/1998 |
| WO | WO-00/67754 A1 | 11/2000 |
| WO | WO-02/22607 A1 | 3/2002 |

(Continued)

OTHER PUBLICATIONS

Green et al. (Journal of Clinical Oncology (2009) vol. 27No. 15S pp. 2565).*
Stathopoutus et al. (Cancer Chemother Pharmacol (2004), vol. 54, pp. 259-264).*
U.S. Appl. No. 15/707,484, Claiborne et al.
A Phase 1 Dose Escalation Study of MLN8237, an Aurora A Kinase Inhibitor, In Adult Patients With Nonhematological Malignancies, Followed by Phase 2 of MLN8237 in Lung, Breast, Head and Neck, or Gastroesophageal Malignancies, <http://clinicaltrials.gov/archive/NCTO (2012).
A Phase 2 Study of MLN9237, a Novel Aurora A Kinase Inhibitor, in the Treatment of Patients with Platinum-Refractory or Platinum-Resistant Epithelial Ovarian, Fallopian Tube, or Primary Peritoneal Carcinoma, ClinicalTrials.gov, NCT00853307, 3 pages, 2011.

(Continued)

Primary Examiner — Savitha M Rao
Assistant Examiner — Taina D Matos Negron
(74) Attorney, Agent, or Firm — Choate, Hall & Stewart LLP; Kristen C. Buteau

(57) ABSTRACT

Disclosed are methods for the treatment of various cell proliferative disorders. Disclosed in particular are methods for treatment of various cell proliferative disorders by administering a selective inhibitor of Aurora A kinase in combination with taxane-based chemotherapy, such as paclitaxel or docetaxel.

16 Claims, 3 Drawing Sheets

(56) References Cited

FOREIGN PATENT DOCUMENTS

| | | |
|---|---|---|
| WO | WO-02/066461 A1 | 8/2002 |
| WO | WO-02/068415 A1 | 9/2002 |
| WO | WO-2002/072073 A2 | 9/2002 |
| WO | WO-02/094834 A1 | 11/2002 |
| WO | WO-03/013545 A1 | 2/2003 |
| WO | WO-2005/037843 A1 | 4/2005 |
| WO | WO-2005/076987 A2 | 8/2005 |
| WO | WO-2005/111039 A2 | 11/2005 |
| WO | WO-2006/055831 A2 | 5/2006 |
| WO | WO-2006/070198 A1 | 7/2006 |
| WO | WO-2007/0076348 A2 | 7/2007 |
| WO | WO-2007/080601 A1 | 7/2007 |
| WO | WO-2007/0104785 A2 | 9/2007 |
| WO | WO-2008/021038 A2 | 2/2008 |
| WO | WO-2008/054808 A2 | 5/2008 |
| WO | WO-2008/063525 A1 | 5/2008 |
| WO | WO-2008/118331 A2 | 10/2008 |
| WO | WO-2009/070652 A1 | 6/2009 |
| WO | WO 2009/114703 * | 9/2009 |
| WO | WO-2009/158687 A1 | 12/2009 |
| WO | WO-2011/103089 A1 | 8/2011 |
| WO | WO-2013/142491 A1 | 9/2013 |

OTHER PUBLICATIONS

A Randomized Phase 2 Study of MLN8237, an Aurora A Kinase Inhibitor, or No. MLN8237 in Patients with Castration-Resistant Prostate Cancer Receiving a Standard Docetaxel/Prednisone Regimen, Preceded by a Phase 1 Dose-Escalation Study, Clinical Trials NCT01094288, (2010).

Alvarez, R.H. et al., MLN8237 (alisertib), an Investigational Aurora A Kinase inhibitor, in patients with breast cancer: Emerging phase 2 results, Cancer Research, 72(24 suppl. 3): 543s, 6 pages, (2012).

Author Not Known, A Randomized Phase 2 Study of MLN8237, an Aurora A Kinase Inhibitor, Plus Weekly Paclitaxel or Weekly Paclitaxel Alone in Patients With Recurrent Epithelial Ovarian, Fallipian Tube, or Primary Peritoneal Cancer, Preceded by a Phase 1 Portion in Patients With Ovarian or Breast Cancer, Clinical Trials NCT01091428, (2010).

Berdnik, D. et al., Drosophila aurora-A is required for centrosome maturation and actin-dependent asymmetirc protein localization during mitosis, Current Biology, 12:640-647 (2002).

Berge, S. et al., Pharmaceutical Salts, Journal of Pharmaceutical Sciences, 66(1):1-19 (1977).

Bischoff, J.R. et al., A homologue of Drosophila aurora kinase is oncogenic and amplified in human colorectal cancers, European Molecular Biology Organization, 17(11):3062-3065 (1998).

Bookman, M.A., Dose-dense chemotherapy in advanced ovarian cancer, The Lancet, 374:1303-1305 (2009).

Cancer Prevention Overview, <http://www.cancer.gov/cancertopics/pdq/prevention/overview/patient>, National Cancer Institute, 2 pages, retrieved on Apr. 9, 2010.

Cantor, E.H. et al., Interaction of calcium channel blockers with non-neuronal benzodiazepine binding sites, Proceedings of the National Academy of Sciences, 81:1549-1552 (1984).

Carmena, M. et. al., The Cellular Geography of Aurora Kinases, Nature, 4:842-854 (2003).

Carol, H. et al., Efficacy and pharmacokinetic/pharmacodynamic evaluation of the Aurora kinase A inhibitor MLN8237 against preclinical models of pediatric cancer, Cancer Chemother Pharmacology. 68:1291-1304 (2011).

Carvajal, R. et al., Aurora kinases: new targets for cancer therapy, Clinical Cancer Research 12(23):6869-6875 (2006).

Cervantes, A. et al, Phase I pharmacokinetic/pharmacodynamic study of MLN8237, an investigational, oral, selective aurora a kinase inhibitor, in patients with advanced solid tumors, Clin. Cancer Res., 18(17):4764-74 (2012).

Cervantes, A. et al., Pharmacokinetic (PK) and pharmacodynamic (PD) results from 2 phase 1 studies of the investigational selective Aurora A kinase (AAK) inhibitor MLN8237: Exposure-dependent AAK inhibition in human tumors, American Society of Clinical Oncology, poster, (2010).

Cervantes, A. et al., Phase 1 Pharmacokinetic and Pharmacodynamic Study of MLN8237, a Novel, Selective Aurora A Kinase Inhibitor, in Patients with Advanced Solid Tumors, American Society of Clinical Oncology, abstract and poster, 6 pages, (2009).

Chiattone, C. et al., MLN8237 (alisertib), an investigational selective inhibitor of aurora a kinase, versus investigators choice of pralatrexate or gemcitabine in patients with relapsed/refractory peripheral T-cell lymphoma: a phase 3 study, Rev. Bras. Hematol. Hemoter., 34(Supl. 2): 300-301(2012).

Dees, C.E. et al., Phase 1 study of the investigational drug MLN8237, an oral Aurora A kinase inhibitor, in patients with solid tumors, American Society of Clinical Oncology, powerpoint, 17 pages, (2010).

Dees, E. C. et al., Phase I study of the investigational drug MLN9237, an Aurora A kinase (AAK) inhibitor, in patients (pts) with solid tumors, Journal of Clinical Oncology, 28(15): 3010-Abstract (2010).

Dees, E.G. et al, Phase I evaluation of MLN 8237, a novel Aurora A kinase inhibitor, Abstract from Chemotherapy Foundation Symposium XXVI Nov. 2008.

Dees, E.C. et al, Phase I study of aurora A kinase inhibitor MLN8237 in advanced solid tumors: safety, pharmacokinetics, pharmacodynamics, and bioavailability of two oral formulations, Clin. Cancer Res., (17):4775-84 (2012).

Development Pipeline Presentations: Abstract Compendium, American Society of Clinical Oncology, 18 pages, (2013).

Diagnosis, Treatment and Management of Gynecologic Disease: Tumor and Kind Tumor, Journal of Japan Society of Obstetrics and Gynecology, 61(12): 637-642 (2009).

Ditchfield, C. et al., Aurora B couples chromosome alignment with anaphase by targeting BubR1, Mad2, and Cenp-E to kinetochores, The Journal of Cell Biology, 161(2):267-280 (2003).

Dutertre, D. et al., On the role of aurora-A in centrosome function, Oncogene, 21:6175-6183 (2002).

Ecsedy, J. et al, Pharmacokinetics (PK), pharmacodynamics (PD) and exposure-PD relationships of the investigational drug MLN8237, an aurora A kinase inhibitor in patients with advanced solid tumors, Clinical Pharmacology & Therapeutics, 89 (Suppl. 1) S67 (2011).

Extended European Search Report for 13189935.3, 9 pages (dated Mar. 19, 2014).

Extended European Search Report for EP15155821, 4 pages (dated Sep. 4, 2015).

Falchook, G. et al., Phase I/II study of weekly paxlitaxel with or without MLN8237 (alisertib), an investigational aurora kinase inhibitor, in patients with recurrent epthelial ovarian, fallopian tube, or primary peritoneal cancer (OC), or breast cancer (BrC): Phase 1 results, American Soceity of Clinical Oncology, 5021:1-2 (2012).

Falchook, G.S. et al., Food effect study of the investigational Aurora A kinase (AAK) inhibitor MLN8237 (alisertib) in patients with advanced solid tumors, American Society of Clinical Oncology, 1 (2012).

Finch, et al., An Efficient General Route to Furo-, Pyrido- and Thieno-[d][2]benzazepines via Pdo Catalysed Cross Coupling Reactions and Nitrile Ylide Cyclisations, Journal of the Chemical Society Perkin Transactions, 1:1193-1203 (1994).

Friedberg, J. W. et al, Phase II study of alisertib, a selective Aurora A kinase inhibitor, in relapsed and refractory aggressive B- and T-cell non-Hodgkin lymphomas, J. Clin. Oncol., 32(1): 44-50 (2014).

Friedberg, J.W. et al., Multicenter Phase 2 Trial of alisertib (MLN8237), an Investigational Inhibitor of Aurora A Kinase, in Patients with Aggressive B-cell and T-cell NHL, American Society of Clinical Oncology, powerpoint, 29 pages (2011).

Gautschi, O. et al., Aurora kinases as anticancer drug targets, Clinical Cancer Research, 14(6):1639-1648 (2008).

Goldberg, S.L. et al., Phase 2 study of MLN8237, an investigational Aurora A Kinase inhibitor in patients with acute myelogenous leukemia or myelodysplastic syndromes, The American Society of Hematology, (2010).

(56) References Cited

OTHER PUBLICATIONS

Görgün, G. et al., A Novel Aurora A Kinase Inhibitor MLN8237 Induces Cytotoxicity and CELL Cycle Arrest in Multiple Myeloma, The American Society of Hematology, 3830:1-2 (2009).
Görgün, G. et al., A novel Aurora-A kinase inhibitor MLN8237 induces cytotoxicity and cell-cycle arrest in multiple myeloma, Lymphoid Neoplasia: Blood, 115(25):5202-5213 (2010).
Hanh, N.M. et al., MLN8237 (alisertib), an investigational Aurora A kinase (AAK) inhibitor, in patients with advanced solid tumors including castration-resistant prostate cancer (CRPC) receiving a standard docetaxel regimen: Preliminary phase 1 results, European Society for Medical Oncology, 1 (2012).
Harrington, E.A. et al., VX-680, a potent and selective small-molecular inhibitor of the Aurora kinases, suppresses tumor growth in vivo, Nature Medicine, 10(3):262-267 (2004).
Hauf, S. et al., The small molecule Hesperadin reveals a role for Aurora B in correcting kinetochore-microtubule attachment and in maintaining the spindle assembly checkpoint, The Journal of Cell Biology, 161(2):281-294 (2003).
Hoar, K et al., MLN8054, a small-molecule inhibitor of aurora A, causes spindle pole and chromosome congression defects leading to aneuploidy, Molecular and Cellular Biology, 27(12):4513-4525 (2007).
Huck, J.J. et al., Antitumor Activity of the Aurora A Inhibitor MLN8237 Combination with Docetaxel in Xenograft Models of Breast and Prostate Cancer, American Association for Cancer Research, 1 (2009).
Huck, J.J. et al., Antitumor Activity of the Aurora A Inhibitor MLN8237 in Combination with Docetaxel in Xenograft Models of Breast and Prostate Cancer, Department of Oncology Millennium Pharmaceuticals, Inc., poster, (2009).
Infante, J. et al. Phase I study of the safety, pharmacokinetics (PK), and pharmacodynamics (PD) of MLN8237, a selective Aurora A kinase inhibitor, in the United States, Eur. J. Cancer, 6(12):90-91 (Suppl) (2008).
International Search Report for PCT/US2005/016445, 4 pages (dated Dec. 7, 2005).
International Search Report for PCT/US2007/023948, 6 pages (dated May 8, 2008).
International Search Report for PCT/US2013/032962, 5 pages (dated Jun. 6, 2013).
Jones, S.F. et al., Phase I clinical trial of MLN8054, a selective inhibitor of aurora A kinase, Journal of Clinical Oncology, ASCO Annual Meeting Proceedings Part 1, 25(18S):3577 (2007).
Katsumata, N. et al., Dose-denase paclitaxel once a week in combination with carboplatin every 3 weeks for advances ovarian cancer: a phase 3, open-label, randomised controlled trial, Lancet, 374:1331-1338 (2011).
Kelly, K. et al., Results from a Phase 1 Multicenter Trial of Alisertib (MLN8237)—An Investigational Aurora A Kinase Inhibitor—in Patients with Advanced Hematologic Malignancies, Blood, 118(21):1061-1062 (2011).
Kelly, K.R. et al., Results from a phase 1 multicenter trial of alisertib (MLN8237)—an investigational Aurora A kinase inhibitor—in patients with advanced hematologic malignancies, American Society of Clinical Oncology, 1 (2011).
Kim, W.S. et al., Phase I Study of MLN9237 (Alisertib) in Adult East Asian Patients (pts) with Advanced Solid Tumors or Lymphomas, Annals of Oncology 24 (Supplement 9): ix31-ix65(2013).
Kollareddy, M. et al., Aurora kinase inhibitors: Progress towards the clinic, Springer: Invest New Drugs, 30:2411-2432 (2012).
Kovar, H., AURKA Inhibitors: Right in Time, Pediatric Blood & Cancer, 55(1):3-4 (2010).
Le, K. et al., Evaluation of optimal dosing regimens for investigational drug MLN8237, an Aurora A kinase inhibitor, in combination with docetaxel through pharmacokinetic-pharmacodynamic (PK-PD) modeling of hematological toxicity, Preclinical Neutropenia Modeling Poster and abstract, 29 pages (2011).
Lee, P., et al. Phase 1/2 study of the investigational Aurora A Kinase (AAK) inhibitor MLN8237 (alisertib) in patients (pts) with non-small cell lung cancer (NSCLC), small cell lung cancer (SCLC), breast cancer (BrC), head/neck cancer (H&N), and gastroesophageal (GE) adenocarcinoma: Preliminary phase 2 results, ASCO (2012).
Mahadevan, D. et al., Targeting Aurora Kinase in Aggressive B-Cell Non-Hodgkin's Lymphomas, The American Society of Hematology, 284:1-2 (2009).
Mahedevan, D. et al., Clinical and Laboratory Evaluation of MLN8237, and Investigational Aurora A Kinase (AAK) Inhibitor, for Treatment of Aggressive Non-Hodgkin's Lymphoma, Peripheral T-cell Lymphomas Symposium, (2011).
Manfredi, M. G. et al., Characterization of Alisertib (MLN8237), an investigational Small-Molecule Inhibitor of Aurora A Kinase Using Novel In Vivo Pharmacodynamic Assays, Clinical Cancer Research, 17(24): 7614-7624 (2011).
Manfredi, M.G. et al., Antitumor activity in MLN8054, an orally active small-molecule inhibitor of aurora A kinase, Proceedings of the National Academy of Sciences USA, 104(10):4106-4111 (2007).
Matulonis, U.A. et al., Phase II study of MLN8237 (alisertib), an investigational Aurora A kinase inhibitor, in patients with platinum-resistant or -refractory epithelial ovarian, fallopian tube, or primary peritoneal carcinoma. Gynecol Oncol.,127(1):63-9 (2012).
Matulonis, U.A. et al., Single-agent activity and safety of teh investigational Aurora A kinase inhibitor MLN8237 in patients with platinum-treated epithelial ovarian, fallopian tube, or primary peritoneal carcinoma, American Society of Clinincal Oncology, poster, (2010).
Mazumdar, A. et al, Aurora Kinase A Inhibition and Paclitaxel as Targeted Combination Therapy for Head and Neck Squamous Cell Carcinoma, Head Neck, 31(5): 625-634 (2009).
Melichar, B. et al., MLN8237 (alisertib), an investigational Aurora A kinase inhibitor, in patients with non-small cell lung cancer, small cell lung cancer, breast cancer, head and neck squamous cell carcinoma, and gastroesophageal cancer: Emerging phase 2 results, American Society of Clinical Oncology, poster, (2012).
Melichar, B. et al., Phase 1/2 study of investigational Aurora A Kinase inhibitor MLN8237 (alisertib): Updated phase 2 results in patients with small lung cancer (SCLC), non-SCLC (NSCLC), breast cancer (BrC), head and neck squamous cell carcinoma (HNSCC), and gastroesophageal cancer (GE), American Society of Clinical Oncology, abstract and poster, 4 pages, (2013).
Meraldi, P. et al., Aurora-A overexpression reveals tetraploidization as a major route to centrosome amplification in $p534^{-/-}$ cells, The European Molecular Biology Organization Journal, 21(4):483-492 (2002).
Mosse, Y.P. et al., Pediatric Phase 1 Trial and Pharmacokinetic Study of MLN8237, an Oral Selective Small Molecule Inhibitor of Aurora A Kinase: A Children's Oncology Group Phase 1 Consortium Study, American Society of Clinical Oncology, poster, (2010).
Mossé, Y. P. et al, Pediatric Phase I Trial and Pharmacokinetic Study of MLN8237, an Investigational Oral Selective Small-Molecule Inhibitor of Aurora Kinase A: A Children's Oncology Group Phase I Consortium Study, Clinical Cancer Res., 18(21): 6058-6064 (2012).
Nawrocki, S.T. et al., The Aurora Kinase Inhibitor MLN8237 has Potent Anticancer Activity in CML and Ph+ ALL Models and Significantly Increases the Efficacy of Nilotinib, Blood, 112:1-2 (2008).
Nippon Rinsho, Chemotherapy for esophageal cancer, 69(6): 342-347 (2011).
O'Connor, O.A. et al., Phase 3 Study of investigational MLN8237 vs. investigator's choice in patients with relapsed/refractory peripheral t-cell lymphoma, American Society of Clinical Oncology, abstract and poster, 7 pages, (2012).
Padmanabhan, S. et al, Phase I Study of an Investigational Aurora A Kinase Inhibitor MLN8237 in Patients with Advanced Hematologic Malignancies, Blood, ASH Annual Meeting Abstracts, 116(21): Abstract 2799, 1154 (2010).
Padmanabhan, S. et al., Phase I Study of an investigational Aurora A Kinase inhibitor MLN8237 in patients with advanced hematologic malignancies, American Society of Clinical Oncology, poster, (2010).

(56) References Cited

OTHER PUBLICATIONS

Qi, W. et al, Aurora Inhibitor MLN8237 in Combination with Docetaxel Enhances Apoptosis and Antitumor Activity in Mantle Cell Lymphoma, Biochem. Pharmacol. 81(7): 881-890 (2011).
Randomized Phase 2 Study of MLN8237, an Aurora A Kinase Inhibitor, Plus Weekly Paclitaxel or Weekly Paclitaxel Alone in Patients With Recurrent Epithelial Ovarian, Fallipian Tube, or Primary Peritoneal Cancer, Preceded by a Phase 1 Portion in Patients With Ovarian or Breast Cancer, <http://clinicaltrials.gov/archive/NCTO> (2011).
Rose, P.G. et al., A phase II trial of weekly paclitaxel and every 3 weeks of carboplatin in potentially platinum-sensitive ovarian and peritoneal carcinoma, Gynecologic Oncology, 96:296-300 (2005).
Sausville, E.A., Aurora kinases dawn as cancer drug targets, Nature Medicine, 10(3):234-235 (2004).
Scharer, C. D. et al, Aurora kinase inhibitors synergize with paclitaxel to induce apoptosis in ovarian cancer cells, Journal of Translational Medicine, 6(79): 1-13 (2008).
Sharma, S. et al., Phase 1 dose-escalation study of the investigational Aurora A Kinase Inhibitor MLN8237 as an enteric-coated tablet formulation in patients with non-hematologic malignancies, American Society of Clinical Oncology, poster, (2011).
Solowey, W.E. et al., Peripheral-Acting Benzodiazepines Inhibit the Growth of Human Melanoma Cells and Potentiate the Antiproliferative Activity of Recombinant Human Interferons, The Journal of Interferon Research, 10(3):269-280 (1990).
Tabernero, C.J. et al., MLN8237, an oral selective Aurora A kinase inhibitor: initial results of dose-finding pharmacokinetic-pharmacodynamic phase I study, Eur. J. Cancer, 6:(92 Suppl) (2008).
Third Party Opposition against CR 2014-0544, 7 pages (Apr. 24, 2015). [English translation, 8 pages].
Vankayalapati, H. et al., Targeting Aurora2 Kinase in Oncogenesis: A Structural Bioinformatics Approach to Target Validation and Rational Drug Design, Molecular Cancer Therapeutics, 2:283-294 (2003).
Venkatakrishnan, K. et al., Clinical pharmacologic considerations for the phase 2/3 dose/regimen of the investigational Aurora A kinase inhibitor MLN8237 (alisertib): Pharmacokinetics, pharmacodynamics, and exposure-safety relationships, American Society of Clinical Oncology, poster, (2012).
Venkatakrishnan, K. et al., Recommended phase 2 dose selection for investigational Aurora A kinase inhibitor MLN8237 (alisertib) combined with paclitaxel: Clinical pharmacokinetics (PK), drug-drug interaction (DDI) assessment and translational exposure efficacy-modeling, poster presented at American Society of Clinical Oncology, Chicago, IL, (May 31-Jun. 4, 2013).
Wang, J.K.T. et al., Benzodiazepines that bind at peripheral sites inhibit cell proliferation, Proceedings of the National Academy of Sciences, 81:753-756 (1984).
Wang,T. et al., A Phase II study of weekly paclitaxel and epirubicin in recurrent or refractory squamous cell carcinoma of the head and neck, Japanese Journal of Clinical Oncology, 38(7):459-463 (2006).
Warner, S.L. et al., Targeting aurora-2 kinase in cancer, Molecular Cancer Therapeutics, 2:589-595 (2003).
Written Opinion for PCT/US2005/016445, 6 pages (dated Dec. 7, 2005).
Written Opinion for PCT/US2007/023948, 9 pages (dated May 8, 2005).
Written Opinion for PCT/US2013/032962, 7 pages (dated Jun. 6, 2013).
Xia, W. et al., Tumor selective G2/M cell cycle arrest and apoptosis of epithelial and hematological malignancies by BBL22, a benzazepine, Proceedings of the National Academy of Sciences, 97(13):7494-7499 (2000).
Yamamoto, N. et al., Phase II Study of Weekly Paclitaxel for Relapsed and Refractory Small Cell Lung Cancer, Anticancer Research, 26(1):777-781 (2006).
Zhang, M. et al., Aurora A Kinase Inhibitor MLN8237 in Combination with Docetaxel Induces Synergistic Antitumor Activity in Triple-Negative Breast Cancer Xenograft Models, EORTC, (2010).
Zhou, H. et al., Tumor amplified kinase STK15/BTAK induces centrosome amplification, aneuploidy and transformation, Nature Genetics, 20:189-193 (1998).
Zhou, X. et al., Pharmacokinetics, Pharmacodynamics and Exposure-Pharmacodynamic Relationships of Investigational Drug MLN8237, and Aurora A Kinase Inhibitor in Patients with Advanced Solid Tumors, American Society Clinical Pharmacology Therapeutics, 1-10 (2011).
U.S. Appl. No. 15/996,166, Claiborne et al.
Reagan-Shaw, S. et al, Dose translation from animal to human studies revisited, FASEB J., 22(3): 659-661 (2008).

* cited by examiner

METHODS OF TREATING CANCER USING AURORA KINASE INHIBITORS

FIELD

This invention relates to methods for the treatment of various cell proliferative disorders. In particular, the invention provides methods for treatment of various cell proliferative disorders by administering a selective inhibitor of Aurora A kinase in combination with taxane-based chemotherapy, such as paclitaxel, or docetaxel.

BACKGROUND

Cancer is the second most common cause of death in the U.S. and accounts for one of every eight deaths worldwide. During 2010, the American Cancer Society estimated approximately 1,529,560 new cancer cases would be diagnosed in the U.S. alone, and an estimated 569,490 Americans would die from cancer. In 2008, an estimated 12.4 million new cancer cases were diagnosed, and 7.6 million people died from cancer worldwide. Although medical advances have improved cancer survival rates, there is a continuing need for new and more effective treatment.

Cancer is characterized by uncontrolled cell reproduction. Antimitotic agents and antimicrotubule agents have been explored as targets for cancer therapy because of their important role in the cell division cycle. The cell division cycle, which regulates the transition from quiescence to cell proliferation comprises four phases: G1, S phase (DNA synthesis), G2, and M phase (mitosis). Non-dividing cells rest in quiescent phase, G0. Inhibition of the mitotic machinery results in a diverse array of outcomes, primarily leading to cell death or arrest.

As the effect of antimitotic agents is not limited to cancer cells alone, the dose-limiting toxicities of these drugs in a clinical setting frequently manifest in rapidly dividing tissue and in the case of antimicrotubule agents are often accompanied by severe peripheral neuropathy in the case of antimicrotubule agents. Therefore, the narrow therapeutic index of antimitotic agents necessitates an understanding of the mechanism of action of these drugs to maximize the chances of rational development of these therapies.

Traditional antimitotic agents include those that directly interfere with microtubule dynamics, essential for mitotic spindle assembly and the subsequent alignment and segregation of DNA to daughter cells. Antimicrotubule agents, such as Taxanes are currently being used in clinical setting. For example, paclitaxel and docetaxel have a similar spectrum of clinical activity including ovarian, lung, breast, bladder, and prostate cancers.

Taxanes stabilize microtubules by altering the kinetics of microtubule depolymerization. In mammalian cells grown in culture, high concentrations of paclitaxel cause the stabilization of aggregated microtubules (Schiff and Horwitz (1980) Proc Natl Acad Sci USA 77:1561-1565). At lower concentrations that resemble exposures achieved in clinical settings, the primary effect of paclitaxel is to stabilize microtubules, and thereby dampen the dynamic instability of microtubules that is a requisite for efficient spindle assembly. As a result of this dampening, microtubules are unable to grow and shrink rapidly, and their ability to bind to condensed chromosomes during mitosis is compromised. Efficient chromosome alignment is thus affected, and this failure of chromosome alignment leads to mitotic delays mediated via the spindle assembly checkpoint.

The spindle assembly checkpoint ensures that chromosomes are properly aligned to the metaphase plate prior to the anaphase initiation where sister chromatids segregate to opposite poles. Interestingly, at low concentrations of paclitaxel, inefficient chromosome alignment has been shown to occur without prolonged mitotic arrest, and the effect of paclitaxel is thus not dependent on its ability to induce mitotic arrest or delays (Chen and Horwitz (2002) Cancer Res 62:1935-1938); Kelling et al. (2003) Cancer Res 63:2794-2801).

For paclitaxel as well as its analog docetaxel, in vitro studies have demonstrated the presence of abnormal DNA contents and cell death even at concentrations where prolonged mitotic arrest does not occur (Chen and Horwitz (2002) Cancer Res 62:1935-1938; Hernandez-Vargas et al. (2007) Cell Cycle 6:780-783; Hernandez-Vargas et al. (2007) Cell Cycle 6:2662-2668. Consistent with this finding, preclinical studies in xenograft models have failed to demonstrate a clear relationship between the degree of mitotic arrest and tumor growth inhibition (Gan et al. (1998) Cancer Chemother Pharmacol 42:177-182; Milross et al. (1996) J Natl Cancer Inst 88:1308-1314; Schimming et al. (1999) Cancer Chemother Pharmacol 43:165-172), and similar findings have been reported in a clinical setting (Symmans et al. (2000) Clin Cancer Res 6:4610-4617).

It has been well established that antimitotic compounds compromise the ability of cells to execute a successful division. Cells will either fail to divide with a prolonged mitotic arrest that leads directly to cell death, or they divide abnormally, with an unequal distribution of DNA (Gascoigne and Taylor (2008) Cancer Cell 14:111-122; Rieder and Maiato (2004) Dev Cell 7:637-651; Weaver and Cleveland (2005) Cancer Cell 8:7-12). Following such an unsuccessful division, cells may continue to cycle or undergo cell-cycle arrest or death. This diversity of outcomes following treatment with antimitotic agents has been shown to be dependent on cell type as well as on concentration of the antimitotic agent used (Gascoigne and Taylor (2008) Cancer Cell 14:111-122; Orth et al. (2008) Mol Cancer Ther 7:3480-3489; Shi et al. (2008) Cancer Res 68:3269-3276).

The prolonged mitotic arrest model suggests that sustained high concentrations of drug are required for antitumor effect. Findings with weekly taxane therapies, which have equivalent efficacy to the once every three weeks taxane therapy schedule, suggest that the same effect can be obtained by splitting the total dose of drug administered.

The toxicities associated with paclitaxel and docetaxel are similar, and include neutropenia as the major dose limiting toxicity, along with significant peripheral neuropathy. In fact, dose reductions are frequent in heavily pretreated patients to mitigate the severity of these toxicities. In clinical studies dose reductions did not reduce the clinical response of the agents, suggesting that the optimal biological dose may be lower than the maximum tolerated dose (Salminen et al., (1999) J Clin Oncol 17:1127). Weekly administration of the taxanes has become more frequently used as clinical data demonstrated less myelosuppression with no decrease in clinical response (Gonzalez-Angulo et al., (2008) J Clin Oncol 26:1585). In breast cancer studies, weekly paclitaxel showed better response rates than once every three weeks dosing (Seidman et al., J Clin Oncol 26:1642 (2008)). However, weekly paclitaxel has demonstrated greater neuropathy than the once every three weeks schedule.

The cell division cycle also involves various protein kinases that are frequently overexpressed in cancer cells. Aurora A kinase, for example, is a key mitotic regulator that is implicated in the pathogenesis of several tumor types. The Aurora kinases, first identified in yeast (Ip11), *Xenopus* (Eg2) and *Drosophila* (Aurora), are critical regulators of mitosis. (*Embo J* (1998) 17, 5627-5637; *Genetics*(1993) 135, 677-691; *Cell* (1995) 81, 95-105; *J Cell Sci* (1998) 111 (Pt 5), 557-572). In humans, three isoforms of Aurora kinase exist, including Aurora A, Aurora B and Aurora C. Aurora A and Aurora B play critical roles in the normal progression of cells through mitosis, whereas Aurora C activity is largely restricted to meiotic cells. Aurora A and Aurora B are structurally closely related. Their catalytic domains lie in the C-terminus, where they differ in only a few amino acids. Greater diversity exists in their non-catalytic N-terminal domains. It is the sequence diversity in this region of Aurora A and Aurora B that dictates their interactions with distinct protein partners, allowing these kinases to have unique subcellular localizations and functions within mitotic cells.

Although Aurora B kinase and Aurora A kinase are both members of the Aurora kinase family, they have distinct roles during the process of mitotic division. In the course of normal mitotic cell division, cells organize bipolar spindles, with two radial arrays of microtubules each focused into a spindle pole at one end, and connected to chromosomes at the other end. In the instant before sister chromatids segregate into daughter cells, the chromosomes are arranged in a straight line (the 'metaphase plate'). This process of organizing bipolar mitotic spindles with fully aligned chromosomes serves to ensure the integrity of a cell's chromosomal complement during mitosis.

The Aurora A gene (AURKA) localizes to chromosome 20q13.2 which is commonly amplified or overexpressed at a high incidence in a diverse array of tumor types. (*Embo J*(1998) 17, 3052-3065; *Int J Cancer* (2006) 118, 357-363; *J Cell Biol* (2003) 161, 267-280; *Mol Cancer Ther* (2007) 6, 1851-1857; *J Natl Cancer Inst* (2002) 94, 1320-1329). Increased Aurora A gene expression has been correlated to the etiology of cancer and to a worsened prognosis. (*Int J Oncol* (2004) 25, 1631-1639; Cancer Res (2007) 67, 10436-10444; *Clin Cancer Res* (2004) 10, 2065-2071; *Clin Cancer Res* (2007) 13, 4098-4104; *Int J Cancer* (2001) 92, 370-373; *Br J Cancer* (2001) 84, 824-831; *J Natl Cancer Inst* (2002) 94, 1320-1329). This concept has been supported in experimental models, demonstrating that Aurora A overexpression leads to oncogenic transformation. (*Cancer Res* (2002) 62, 4115-4122; *Mol Cancer Res* (2009) 7, 678-688; *Oncogene* (2006) 25, 7148-7158; *Cell Res* (2006) 16, 356-366; *Oncogene* (2008) 27, 4305-4314; *Nat Genet* (1998) 20, 189-193). Overexpression of Aurora A kinase is suspected to result in a stoichiometric imbalance between Aurora A and its regulatory partners, leading to chromosomal instability and subsequent transforming events. The potential oncogenic role of Aurora A has led to considerable interest in targeting this kinase for the treatment of cancer.

As a key regulator of mitosis, Aurora A plays an essential role in mitotic entry and normal progression of cells through mitosis. (*Nat Rev Mol Cell Biol* (2003) 4, 842-854; *Curr Top Dev Biol* (2000) 49, 331-42; *Nat Rev Mol Cell Biol* (2001) 2(1), 21-32). During a normal cell cycle, Aurora A kinase is first expressed in the G2 stage where it localizes to centrosomes and functions in centrosome maturation and separation as well as in the entry of cells into mitosis. In mitotic cells Aurora A kinase predominantly localizes to centrosomes and the proximal portion of incipient mitotic spindles. There it interacts with and phosphorylates a diverse set of proteins that collectively function in the formation of mitotic spindle poles and spindles, the attachment of spindles to sister chromatid at the kinetochores, the subsequent alignment and separation of chromosome, the spindle assembly checkpoint and cytokinesis. (*J Cell Sci* (2007) 120, 2987-2996; *Trends Cell Biol* (1999) 9, 454-459; *Nat Rev Mol Cell Biol* (2003) 4, 842-854; *Trends Cell Biol* (2005) 15, 241-250).

Although selective inhibition of Aurora A kinase results in a delayed mitotic entry (*The Journal of biological chemistry* (2003) 278, 51786-51795), cells commonly enter mitosis despite having inactive Aurora A kinase. Cells in which Aurora A kinase has been selectively inhibited demonstrate a variety of mitotic defects including abnormal mitotic spindles (monopolar or multipolar spindles) and defects in the process of chromosome alignment. With time, monopolar and multipolar spindles may resolve to form two opposing spindle poles, although some of these defects may lead immediately to cell death via defective mitoses. While spindle defects resulting from Aurora A kinase inhibition induce mitotic delays, presumably through activation of the spindle assembly checkpoint, cells ultimately divide at a frequency near that of untreated cells. (*Mol Cell Biol* (2007) 27(12), 4513-25; *Cell Cycle* (2008) 7(17), 2691-704; *Mol Cancer Ther* (2009) 8(7), 2046-56.). This inappropriate cell division occurs following a slow-acting suppression of the spindle assembly checkpoint due to loss of Aurora A kinase function. (*Cell Cycle* (2009) 8(6), 876-88). Bipolar spindles that are formed in the absence of Aurora A kinase function frequently show chromosome alignment and segregation defects, including chromosome congression defects at metaphase, lagging chromosomes at anaphase, and telophase bridges.

Consistent with the chromosome segregation defects, cells treated with MLN8054, a selective inhibitor of Aurora A kinase, develop aneuploidy that increases over time. Subsequent to repeated passages through defective mitotic divisions, cells treated with MLN8054 will often undergo senescence, an irreversible growth arrest with distinctive morphological characteristics. (*Mol Cancer Res* (2010) 8(3), 373-84). In some cell lines, MLN8054-treated cells exit from mitosis and activate a p53-dependent postmitotic G1 checkpoint, which subsequently induces p21 and Bax, leading to G1 arrest followed by the induction of apoptosis. (*Mol. Cancer Ther* (2009) 8(7), 2046-56). Some cells may also exit mitosis without cytokinesis. These cells enter the G1 phase of the cell cycle with double the normal DNA content and are therefore referred to as G1 tetraploid cells. Lastly, some cells may divide, albeit with severe chromosome segregation defects (*Mol Cell Biol* (2007) 27(12), 4513-25). In the latter two outcomes, the abnormal mitotic divisions result in deleterious aneuploidy leading to cell death or arrest. Alternatively, it is possible that a portion of these cells may be resistant to these terminal outcomes and can reenter the cell cycle, as aneuploidy has been demonstrated to be both a suppressor and a promoter of tumor cell growth.

Given the importance of the protein kinases involved in driving the cell cycle, it would be beneficial if more effective treatment regimens, which target these kinases could be developed. In particular, combined treatment regimens with antimitotics could be helpful for patients suffering from cell proliferative disorders, and might potentially even decrease the rate of relapse or overcome the resistance to a particular anticancer agent sometimes seen in these patients.

Drug tolerability and the prevalence of side effects are important considerations in structuring dose and schedule selection for the treatment of cell proliferative disorders. For example, treatments that require the use of therapeutic agents, for example, taxanes, that result in severe adverse events, such as neutropenia, may become ineffective due to insufficient patient compliance or because an effective therapeutic dose cannot be administered to the patient. Similarly, treatments that result in a higher effective concentration of the active ingredient for a longer period of time may provide increased therapeutic efficacy. Thus, there is a need for new cancer treatment regimens, including combination therapies, which avoid or ameliorate harsh side effects resulting from toxicity while providing increased therapeutic efficacy by achieving improved exposure efficacy.

DETAILED DESCRIPTION

1. General Description

Figure 1:
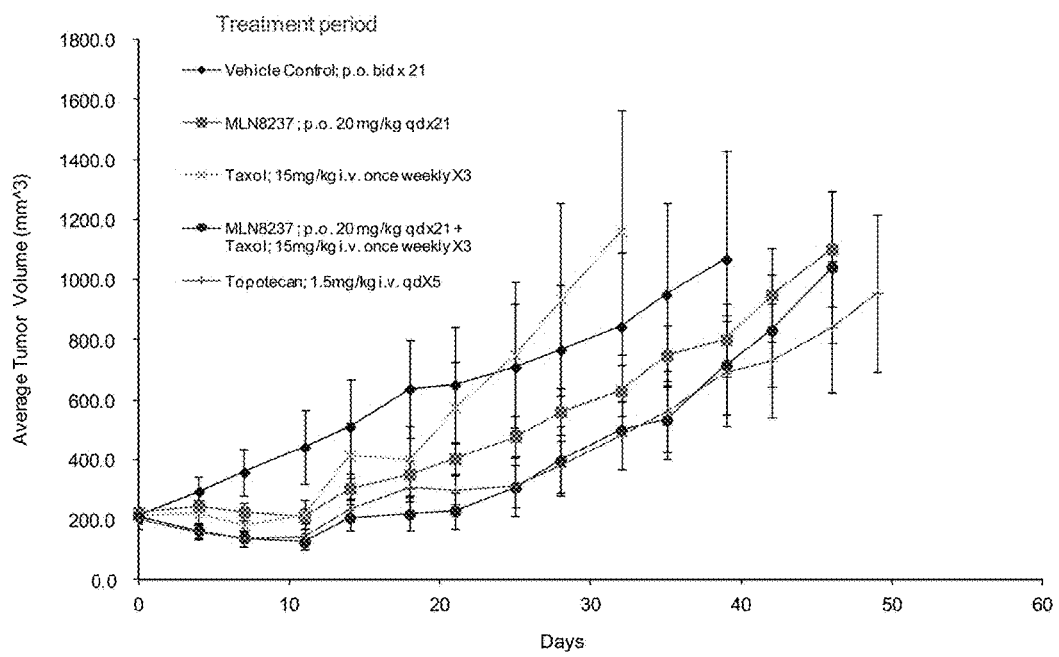
FIG. 1 shows the antitumor activity (average tumor volume as a function of time) of alisertib combined with paclitaxel in the NCI-H69 small cell lung cancer tumor model.

As discussed above, there remains a need to provide alternate therapies for the treatment of cancer, particularly those that avoid or ameliorate the harsh side effects of currently existing therapies. While additive and synergistic antitumor activity has been demonstrated for the combination of selective inhibitors of Aurora A kinase with taxanes, neutropenia is a common dose limiting toxicity.

The present inventors have discovered that decreasing the standard weekly paclitaxel dose from about 80 mg/m$^2$ to about 60 mg/m$^2$ allows achievement of surprisingly higher alisertib (MLN8237) doses with an acceptable tolerability profile without losing efficacy. An alisertib dose of about 10 mg BID (twice daily) was the maximum tolerated dose that could be achieved in combination with the standard weekly dose of about 80 mg/m$^2$ of paclitaxel. Unexpectedly, much higher doses of up to about 40 mg BID of alisertib were tolerated in combination with paclitaxel when the dose of weekly paclitaxel was reduced to about 60 mg/m$^2$.

Accordingly, the present invention relates to methods for the treatment of cell proliferative disorders comprising administering to a patient in need thereof a selective inhibitor of Aurora A kinase with the concomitant or sequential administration of a taxane, such as paclitaxel or docetaxel, wherein the amounts of each agent are therapeutically effective when used in combination.

2. Definitions

As used herein, the terms "cell proliferative disorder" and "cancer" refer to a cellular disorder characterized by uncontrolled or disregulated cell proliferation, decreased cellular differentiation, inappropriate ability to invade surrounding tissue, and/or ability to establish new growth at ectopic sites. The terms "cell proliferative disorder" and "cancer" include, but are not limited to, solid tumors and bloodborne tumors. The terms "cell proliferative disorder" and "cancer" encompass diseases of skin, tissues, organs, bone, cartilage, blood, and vessels. The terms "cell proliferative disorder" and "cancer" further encompass primary and metastatic cancers. As used herein, the term "cell proliferative disorders" includes, but is not limited to, cancerous hyperproliferative disorders (e.g., brain, lung, squamous cell, bladder, gastric, pancreatic, breast, head, neck, renal, liver, kidney, ovarian, prostate, colorectal, colon, epidermoid, esophageal, testicular, gynecological or thyroid cancer, acute myeloid leukemia, multiple myeloma, mesothelioma, Non-small cell lung carcinoma (NSCLC), neuroblastoma, and acute lymphoblastic leukemia (ALL)); non-cancerous hyperproliferative disorders (e.g., benign hyperplasia of the skin (e.g., psoriasis), restenosis, and benign prostatic hypertrophy (BPH)); and diseases related to vasculogenesis or angiogenesis (e.g., tumor angiogenesis, hemangioma, glioma, melanoma, Kaposi's sarcoma and ovarian, breast, lung, pancreatic, prostate, colon and epidermoid cancer).

As used herein, the term "patient" means an animal, preferably a mammal, and most preferably a human. In some embodiments, the patient has been treated with an agent, e.g., an Aurora A kinase selective inhibitor or a taxane, prior to initiation of treatment according to the method of the invention. In some embodiments, the patient is a patient at risk of developing or experiencing a recurrence of a proliferative disorder.

The expressions "therapeutically effective" and "therapeutic effect" refer to a benefit including, but not limited to, the treatment or amelioration of symptoms of a proliferative disorder discussed herein. It will be appreciated that the therapeutically effective amount or the amount of agent required to provide a therapeutic effect will vary depending upon the intended application (in vitro or in vivo), or the subject and disease condition being treated (e.g., nature of the severity of the condition to be treated, the particular inhibitor, the route of administration and the age, weight, general health, and response of the individual patient), which can be readily determined by a person of skill in the art. For example, an amount of a selective inhibitor of Aurora A kinase in combination with an amount of a taxane is therapeutically effective if it is sufficient to effect the treatment or amelioration of symptoms of a proliferative disorder discussed herein.

The expressions "prophylactically effective" and "prophylactic effect" refer to a benefit including, but not limited to, the prophylaxis of symptoms of a proliferative disorder discussed herein. It will be appreciated that the prophylactically effective amount or the amount of agent required to provide a prophylactic effect will vary depending upon the intended application (in vitro or in vivo), or the subject and disease condition being prevented (e.g., nature of the severity of the condition to be prevented, the particular inhibitor, the route of administration and the age, weight, general health, and response of the individual patient), which can be readily determined by a person of skill in the art. For example, an amount of a selective inhibitor of Aurora A kinase in combination with an amount of a taxane is prophylactically effective if it is sufficient to effect the prophylaxis of symptoms of a proliferative disorder discussed herein.

As used herein, the term "Aurora A kinase" refers to a serine/threonine kinases involved in mitotic progression. Aurora A kinase is also known as AIK, ARK 1, AURA, BTAK, STK6, STK7, STK15, AURORA2, MGC34538, and AURKA. A variety of cellular proteins that play a role in cell division are substrates for phosphorylation by the Aurora A kinase enzyme, including, without limitation, p53, TPX-2, XIEg5 (in *Xenopus*), and D-TACC (in *Drosophila*). The Aurora A kinase enzyme is also itself a substrate for autophosphorylation, e.g., at Thr288. Preferably, the Aurora A kinase is a human Aurora A kinase.

The term "inhibitor of Aurora A kinase" or "Aurora A kinase inhibitor" is used to signify a compound that is capable of interacting with Aurora A kinase and inhibiting its enzymatic activity.

Inhibiting Aurora A kinase enzymatic activity means reducing the ability of Aurora A kinase to phosphorylate a substrate peptide or protein. In various embodiments, such reduction of Aurora A kinase activity is at least about 75%, at least about 90%, at least about 95%, or at least about 99%. In various embodiments, the concentration of Aurora A kinase inhibitor required to reduce an Aurora A kinase enzymatic activity is less than about 1 µM, less than about 500 nM, less than about 100 nM, or less than about 50 nM. Preferably, the concentration that is required to inhibit the enzymatic activity of Aurora A kinase is lower than the concentration of the inhibitor that is required to inhibit the enzymatic activity of Aurora B kinase. In various embodiments, the concentration of an Aurora A kinase inhibitor that is required to reduce Aurora A kinase enzymatic activity is at least about 2-fold, at least about 5-fold, at least about 10-fold, at least about 20-fold, at least about 50-fold, at least about 100-fold, at least about 500-fold, or at least about 1000-fold lower than the concentration of the inhibitor that is required to reduce Aurora B kinase enzymatic activity.

Inhibition of Aurora A and inhibition of Aurora B result in markedly different cellular phenotypes. (*Proc. Natl. Acad. Sci.* (2007) 104: 4106; *Mol Cancer Ther* (2009) 8(7), 2046-56; *Chem Biol.* (2008) 15(6) 552-62). For example, inhibition of Aurora A in the absence of Aurora B inhibition results in increased mitotic index as measured by quantifying phosphorylated histone H3 on serine 10 (pHisH3). pHisH3 is a unique substrate of Aurora B in physiological systems (e.g. intact cells). By contrast, inhibition of Aurora B or dual inhibition of Aurora A and Aurora B results in a decrease in pHisH3. Accordingly, as used herein, the term "selective inhibitor of Aurora A kinase" or "selective Aurora A kinase inhibitor" refers to an inhibitor that exhibits an Aurora A kinase inhibitor phenotype at effective antitumor concentrations. In some embodiments, the selective Aurora A kinase inhibitor causes a transient mitotic delay, as measured by quantification of pHisH3, when administered to mice at a dose where the free fraction adjusted concentration ($C_{ave}$) in plasma is equivalent to the free fraction adjusted concentration achieved in plasma in humans at the maximum tolerated dose (MTD). As used herein, "free fraction adjusted concentration" refers to the plasma concentration of free drug (not protein bound).

As used herein, the term "taxane" refers to a class of diterpenes produced by the plants of the genus *Taxus* (yews). Examples of taxanes include, but are not limited to, paclitaxel (TAXOL®), docetaxel (TAXOTERE®), and ABRAXANE® (Paclitaxel Injection).

As used herein, the term "in combination" refers to use of both a selective Aurora A kinase inhibitor and a taxane in the treatment of the same disease or condition in the same patient. As further described below, unless explicitly specified, the term "in combination" does not restrict the timing of administration of the selective Aurora A kinase inhibitor or the taxane.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

The term "aliphatic" or "aliphatic group", as used herein, means a substituted or unsubstituted straight-chain, branched or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, alkynyl groups and hybrids thereof, such as (cycloalkyl)alkyl, (cycloalkenyl) alkyl or (cycloalkyl)alkenyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring. The term "cycloaliphatic" may be used interchangeably with the terms "carbocycle", "carbocyclyl", "carbocyclo", or "carbocyclic".

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl$(C_{1-6})$alkyl, $C_{6-10}$ aryl$(C_{1-4})$alkyl, or $C_{6-10}$ aryl$(C_{1-3})$alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl) or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, for an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "substituted", as used herein, means that a hydrogen radical of the designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, $-NO_2$, $-CN$, $-R^*$, $-C(R^*)=C(R^*)_2$, $-C\equiv C-R^*$, $-OR^*$, $-SR^\circ$, $-S(O)R^\circ$, $-SO_2R^\circ$, $-SO_3R$, $-SO_2N(R^+)_2$, $-N(R^+)_2$, $-NR^+C(O)R^*$, $-NR^+C(O)N(R^+)_2$, $-NR^+CO_2R^\circ$, $-O-CO_2R^*$, $-OC(O)N(R^+)_2$, $-O-C(O)R^*$, $-CO_2R^*$, $-C(O)-C(O)R^*$, $-C(O)R^*$, $-C(O)N(R^+)_2$, $-C(O)N(R^+)C(=NR^+)-N(R^+)_2$, $-N(R^+)C(=NR^+)-N(R^+)-C(O)R^*$, $-C(=NR^+)-N(R^+)_2$, $-C(=NR^+)-OR^*$, $-N(R^+)-N(R^+)_2$, $-N(R^+)C(=NR^+)-N(R^+)_2$, $-NR^+SO_2R^\circ$, $-NR^+SO_2N(R^+)_2$, $-P(O)(R^*)_2$, $-P(O)(OR^*)_2$, $-O-P(O)-OR^*$, and $-P(O)(NR^+)-N(R^+)_2$; or two adjacent substituents, taken together with their intervening atoms, form a 5-6 membered unsaturated or partially unsaturated ring having 0-3 ring atoms selected from the group consisting of N, O, and S.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —$NO_2$, —CN, —R*, —C(R*)=C(R*)$_2$, —C≡C—R*, —OR*, —SR°, —S(O)R°, —$SO_2$R°, —$SO_3$R°, —$SO_2$N($R^+$)$_2$, —N($R^+$)$_2$, —$NR^+$C(O)R*, —$NR^+$C(O)N($R^+$)$_2$, —$NR^+$CO$_2$R°, —O—CO$_2$R*, —OC(O)N($R^+$)$_2$, —O—C(O)R*, —CO$_2$R*, —C(O)—C(O)R*, —C(O)R*, —C(O)N($R^+$)$_2$, —C(O)N($R^+$)C(=$NR^+$)—N($R^+$)$_2$, —N($R^+$)C(=$NR^+$)—N($R^+$)—C(O)R*, —C(=$NR^+$)—N($R^+$)$_2$, —C(=$NR^+$)—OR*, —N($R^+$)—N($R^+$)$_2$, —N($R^+$)C(=$NR^+$)—N($R^+$)$_2$, —NR+SO$_2$R°, —$NR^+$SO$_2$N($R^+$)$_2$, —P(O)(R*)$_2$, —P(O)(OR*)$_2$, —O—P(O)—OR*, and —P(O)($NR^+$)—N($R^+$)$_2$; or two adjacent substituents, taken together with their intervening atoms, form a 5-6 membered unsaturated or partially unsaturated ring having 0-3 ring atoms selected from the group consisting of N, O, and S.

Each $R^+$, independently, is hydrogen or an optionally substituted aliphatic, aryl, heteroaryl, or heterocyclyl group, or two $R^+$ on the same nitrogen atom, taken together with the nitrogen atom, form a 5-8 membered aromatic or non-aromatic ring having, in addition to the nitrogen atom, 0-2 ring heteroatoms selected from N, O, and S. Each R* independently is hydrogen or an optionally substituted aliphatic, aryl, heteroaryl, or heterocyclyl group. Each R° is an optionally substituted aliphatic or aryl group.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—N(R*)$_2$, =N—OR*, =N—NHC(O)R*, =N—NHCO$_2$R°, =N—NHSO$_2$R°, or =N—R*, where each R* and R° is as defined above.

Suitable substituents on the nitrogen atom of a non-aromatic heterocyclic ring include —R*, —N(R*)$_2$, —C(O)R*, —CO$_2$R*, —C(O)—C(O)R*—C(O)CH$_2$C(O)R*, —SO$_2$R*, —SO$_2$N(R*)$_2$, —C(=S) N(R*)$_2$, —C(=NH)—N(R*)$_2$, and —NR*SO$_2$R*; wherein each R* is as defined above.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

It will be apparent to one skilled in the art that certain compounds described herein may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

3. Detailed Description
Selective Inhibitors of Aurora A Kinase

Any molecule capable of selectively inhibiting the enzymatic activity of Aurora A kinase may be used in the methods, pharmaceutical compositions, and kits of the present invention. In some embodiments the selective Aurora A kinase inhibitor is a small molecular weight compound. In particular, selective inhibitors of Aurora A kinase include the compounds described herein, as well as compounds disclosed in, for example, US Publication No. 2008/0045501, U.S. Pat. No. 7,572,784, WO 05/111039, WO 08/021038, U.S. Pat. No. 7,718,648, WO 08/063525, US Publication No. 2008/0167292, U.S. Pat. No. 8,026,246, WO 10/134965, US Publication No. 2010/0310651, WO 11/014248, US Publication No. 2011/0039826, and US Publication No. 2011/0245234, each of which is hereby incorporated by reference in its entirety, sodium 4-{[9-chloro-7-(2-fluoro-6-methoxyphenyl)-5H-pyrimido[5,4-d][2]benzazepin-2-yl]amino}-2-methoxybenzoate, KW-2449 (Kyowa), ENMD-2076 (EntreMed), and MK-5108 (Vertex/Merck). Also suitable for use in the methods, pharmaceutical compositions, and kits of the invention are solvated and hydrated forms of any of these compounds. Also suitable for use in the methods, pharmaceutical compositions, and kits of the invention are pharmaceutically acceptable salts of any of the compounds, and solvated and hydrated forms of such salts. These selective Aurora A kinase inhibitors can be prepared in a number of ways well known to one skilled in the art of organic synthesis, including, but not limited to, the methods of synthesis described in detail in the references referred to herein.

Aurora A kinase inhibitors can be assayed in vitro or in vivo for their ability to selectively bind to and/or inhibit an Aurora A kinase. In vitro assays include assays to determine selective inhibition of the ability of an Aurora A kinase to phosphorylate a substrate protein or peptide. Alternate in vitro assays quantitate the ability of the compound to selectively bind to an Aurora A kinase. Selective inhibitor binding may be measured by radiolabelling the inhibitor prior to binding, isolating the inhibitor/Aurora A kinase complex and determining the amount of radiolabel bound. Alternatively, selective inhibitor binding may be determined by running a competition experiment in which new inhibitors are incubated with Aurora A kinase bound to a known radioligand. The compounds also can be assayed for their ability to affect cellular or physiological functions mediated by Aurora A kinase activity. In order to assess selectivity for Aurora A kinase over Aurora B kinase, inhibitors can also be assayed in vitro and in vivo for their ability to selectively bind to and/or inhibit an Aurora B kinase, using assays analogous to those described above for Aurora A kinase. Inhibitors can be assayed in vitro and in vivo for their ability to inhibit Aurora A kinase in the absence of Aurora B kinase inhibition, by immunofluorescent detection of pHisH3. (*Proc. Natl. Acad. Sci.* (2007) 104, 4106). Assays for each of these activities are known in the art.

In some embodiments, the selective Aurora A kinase inhibitor is represented by formula (V):

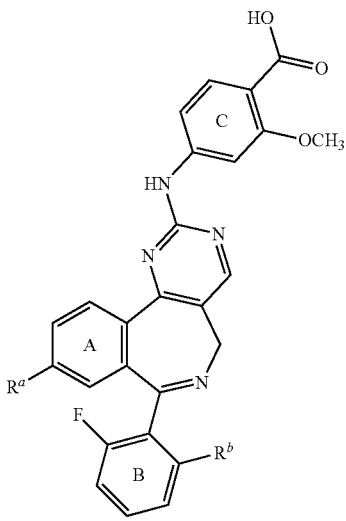

(V)

or a pharmaceutically acceptable salt thereof;
wherein:
$R^a$ is selected from the group consisting of $C_{1-3}$ aliphatic, $C_{1-3}$ fluoroaliphatic, —$R^1$, -T-$R^1$, —$R^2$, and -T-$R^2$;
T is a $C_{1-3}$alkylene chain optionally substituted with fluoro;
$R^1$ is an optionally substituted aryl, heteroaryl, or heterocyclyl group;
$R^2$ is selected from the group consisting of halo, —C≡C—$R^3$, —CH═CH—$R^3$, —N($R^4$)$_2$, and —O$R^5$;
$R^3$ is hydrogen or an optionally substituted aliphatic, aryl, heteroaryl, or heterocyclyl group;
each $R^4$ independently is hydrogen or an optionally substituted aliphatic, aryl, heteroaryl, or heterocyclyl group; or two $R^4$ on the same nitrogen atom, taken together with the nitrogen atom form an optionally substituted 5- to 6-membered heteroaryl or 4- to 8-membered heterocyclyl ring having, in addition to the nitrogen atom, 0-2 ring heteroatoms selected from N, O, and S;
$R^5$ is hydrogen or an optionally substituted aliphatic, aryl, heteroaryl, or heterocyclyl group; and
$R^b$ is selected from the group consisting of fluoro, chloro, —CH$_3$, —CF$_3$, —OH, —OCH$_3$, —OCF$_3$, —OCH$_2$CH$_3$, and —OCH$_2$CF$_3$.

In some embodiments, $R^1$ is a 5- or 6-membered aryl, heteroaryl, or heterocyclyl ring optionally substituted with one or two substituents independently selected from the group consisting of halo, $C_{1-3}$ aliphatic, and $C_{1-3}$ fluoroaliphatic. In certain embodiments, $R^1$ is a phenyl, furyl, pyrrolidinyl, or thienyl ring optionally substituted with one or two substituents independently selected from the group consisting of halo, $C_{1-3}$ aliphatic, and $C_{1-3}$ fluoroaliphatic.

In some embodiments, $R^3$ is hydrogen, $C_{1-3}$ aliphatic, $C_{1-3}$ fluoroaliphatic, or —CH$_2$—OCH$_3$.

In some embodiments, $R^5$ is hydrogen, $C_{1-3}$ aliphatic, or $C_{1-3}$ fluoroaliphatic.

In certain embodiments, $R^a$ is halo, $C_{1-3}$ aliphatic, $C_{1-3}$ fluoroaliphatic, —OH, —O($C_{1-3}$ aliphatic), —O($C_{1-3}$ fluoroaliphatic), —C≡C—$R^3$, —CH═CH—$R^3$, or an optionally substituted pyrrolidinyl, thienyl, furyl, or phenyl ring, wherein $R^3$ is hydrogen, $C_{1-3}$ aliphatic, $C_{1-3}$ fluoroaliphatic, or —CH$_2$—OCH$_3$. In certain particular embodiments, $R^a$ is selected from the group consisting of chloro, fluoro, $C_{1-3}$ aliphatic, $C_{1-3}$ fluoroaliphatic, —OCH$_3$, —OCF$_3$, —C≡C—H, —C≡C—CH$_3$, —C≡C—CH$_2$OCH$_3$, —CH═CH$_2$, —CH═CHCH$_3$, N-methylpyrrolidinyl, thienyl, methylthienyl, furyl, methylfuryl, phenyl, fluorophenyl, and tolyl.

Table 1 provides the chemical names for specific examples of compounds of formula (V).

TABLE 1

Examples of Compounds of Formula (V)

| | Chemical Name |
|---|---|
| V-1 | 4-{[9-chloro-7-(2-fluoro-6-methoxyphenyl)-5H-pyrimido[5,4-d][2]benzazepin-2-yl]amino}-2-methoxybenzoic acid |
| V-2 | 4-{[9-ethynyl-7-(2-fluoro-6-methoxyphenyl)-5H-pyrimido[5,4-d][2]benzazepin-2-yl]amino}-2-methoxybenzoic acid |
| V-3 | 4-({9-chloro-7-[2-fluoro-6-(trifluoromethoxy)phenyl]-5H-pyrimido[5,4-d][2]benzazepin-2-yl}amino)-2-methoxybenzoic acid |
| V-4 | 4-{[7-(2-fluoro-6-methoxyphenyl)-9-(1-methyl-1H-pyrrol-2-yl)-5H-pyrimido[5,4-d][2]benzazepin-2-yl]amino}-2-methoxybenzoic acid |
| V-5 | 4-{[7-(2-fluoro-6-methoxyphenyl)-9-(4-methyl-3-thienyl)-5H-pyrimido[5,4-d][2]benzazepin-2-yl]amino}-2-methoxybenzoic acid |
| V-6 | 4-{[7-(2-fluoro-6-methoxyphenyl)-9-(3-methyl-2-furyl)-5H-pyrimido[5,4-d][2]benzazepin-2-yl]amino}-2-methoxybenzoic acid |
| V-7 | 4-({9-ethynyl-7-[2-fluoro-6-(2,2,2-trifluoroethoxy)phenyl]-5H-pyrimido[5,4-d][2]benzazepin-2-yl}amino)-2-methoxybenzoic acid |
| V-8 | 4-{[9-chloro-7-(2,6-difluorophenyl)-5H-pyrimido[5,4-d][2]benzazepin-2-yl]amino}-2-methoxybenzoic acid |
| V-9 | 4-{[7-(2-fluoro-6-methoxyphenyl)-9-(2-methylphenyl)-5H-pyrimido[5,4-d][2]benzazepin-2-yl]amino}-2-methoxybenzoic acid |
| V-10 | 4-{[7-(2-fluoro-6-methoxyphenyl)-9-prop-1-yn-1-yl-5H-pyrimido[5,4-d][2]benzazepin-2-yl]amino}-2-methoxybenzoic acid |
| V-11 | 4-{[7-(2-fluoro-6-methoxyphenyl)-9-vinyl-5H-pyrimido[5,4-d][2]benzazepin-2-yl]amino}-2-methoxybenzoic acid |
| V-12 | 4-{[7-(2-fluoro-6-methoxyphenyl)-9-(2-fluorophenyl)-5H-pyrimido[5,4-d][2]benzazepin-2-yl]amino}-2-methoxybenzoic acid |
| V-13 | 4-{[7-(2-fluoro-6-methoxyphenyl)-9-(3-methoxyprop-1-yn-1-yl)-5H-pyrimido[5,4-d][2]benzazepin-2-yl]amino}-2-methoxybenzoic acid |
| V-14 | 4-({7-(2-fluoro-6-methoxyphenyl)-9-[(1E)-prop-1-en-1-yl]-5H-pyrimido[5,4-d][2]benzazepin-2-yl}amino)-2-methoxybenzoic acid |

TABLE 1-continued

Examples of Compounds of Formula (V)

Chemical Name

V-15  4-({9-chloro-7-[2-fluoro-6-(2,2,2-trifluoroethoxy)phenyl]-5H-pyrimido[5,4-d][2]benzazepin-2-yl}amino)-2-methoxybenzoic acid
V-16  4-{[7-(2-fluoro-6-methoxyphenyl)-9-(2-furyl)-5H-pyrimido[5,4-d][2]benzazepin-2-yl]amino}-2-methoxybenzoic acid
V-17  4-{[9-chloro-7-(2-fluoro-6-hydroxyphenyl)-5H-pyrimido[5,4-d][2]benzazepin-2-yl]amino}-2-methoxybenzoic acid
V-18  4-{[7-(2-fluoro-6-methoxyphenyl)-9-phenyl-5H-pyrimido[5,4-d][2]benzazepin-2-yl]amino}-2-methoxybenzoic acid In one embodiment, the compound of formula (V) is 4-{[9-chloro-7-(2-fluoro-6-methoxyphenyl)-5H-pyrimido[5,4-d][2]benzazepin-2-yl]amino}-2-methoxybenzoic acid (alisertib (MLN8237)), or a pharmaceutically acceptable salt thereof. In another embodiment, the compound of formula (V) is sodium 4-{[9-chloro-7-(2-fluoro-6-methoxyphenyl)-5H-pyrimido[5,4-d][2]benzazepin-2-yl]amino}-2-methoxybenzoate. In yet another embodiment, the compound of formula (V) is sodium 4-{[9-chloro-7-(2-fluoro-6-methoxyphenyl)-5H-pyrimido[5,4-d][2]benzazepin-2-yl]amino}-2-methoxybenzoate monohydrate. In another embodiment, the compound of formula (V) is sodium 4-{[9-chloro-7-(2-fluoro-6-methoxyphenyl)-5H-pyrimido[5,4-d][2]benzazepin-2-yl]amino}-2-methoxybenzoate polymorph Form 2, as described in US Publication No. 2008/0167292, U.S. Pat. No. 8,026,246, and US Publication No. 2011/0245234, each of which is hereby incorporated by reference in their entirety.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also a selective inhibitor of Aurora A kinase.

If a pharmaceutically acceptable salt of the selective inhibitor of Aurora A kinase is utilized in pharmaceutical compositions, the salt preferably is derived from an inorganic or organic acid or base. For reviews of suitable salts, see, e.g., Berge et al, *J. Pharm. Sci.* 66:1-19 (1977) and *Remington: The Science and Practice of Pharmacy.* 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth.

Also, basic nitrogen-containing groups may be quaternized with such agents as lower alkyl halides, such as methyl, ethyl, propyl, and butyl chlorides, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

Dosages and Administration of Selective Inhibitors of Aurora A Kinase in Combination with Taxanes The therapeutically effective amounts or suitable dosages of the selective inhibitor of Aurora A kinase depends upon a number of factors, including the nature of the severity of the condition to be treated, the particular inhibitor, the route of administration and the age, weight, general health, and response of the individual patient. In certain embodiments, the suitable dose level is one that achieves an effective exposure as measured by increased skin mitotic index, or decreased chromosome alignment and spindle bipolarity in tumor mitotic cells, or other standard measures of effective exposure in cancer patients. In certain embodiments, the suitable dose level is one that achieves a therapeutic response as measured by tumor regression, or other standard measures of disease progression, progression free survival or overall survival. In other embodiments, the suitable dose level is one that achieves this therapeutic response and also minimizes any side effects associated with the administration of the therapeutic agent.

Suitable daily dosages of selective inhibitors of Aurora A kinase can generally range, in single or divided or multiple doses, from about 10% to about 100% of the maximum tolerated dose as a single agent. In certain embodiments, the suitable dosages are from about 15% to about 100% of the maximum tolerated dose as a single agent. In some other embodiments, the suitable dosages are from about 25% to about 90% of the maximum tolerated dose as a single agent. In some other embodiments, the suitable dosages are from about 30% to about 80% of the maximum tolerated dose as a single agent. In some other embodiments, the suitable dosages are from about 40% to about 75% of the maximum tolerated dose as a single agent. In some other embodiments, the suitable dosages are from about 45% to about 60% of the maximum tolerated dose as a single agent. In other embodiments, suitable dosages are about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, or about 110% of the maximum tolerated dose as a single agent.

Suitable daily dosages of alisertib can generally range, in single or divided or multiple doses, from about 20 mg to about 120 mg per day. Other suitable daily dosages of alisertib can generally range, in single or divided or multiple doses, from about 40 mg to about 80 mg per day. Other suitable daily dosages of alisertib can generally range, in single or divided or multiple doses, from about 60 mg to about 80 mg per day. In certain embodiments, the suitable dosages are from about 10 mg twice daily to about 40 mg twice daily. In some other embodiments, the suitable dosages are from about 20 mg twice daily to about 40 mg twice daily. In some other embodiments, the suitable dosages are from about 30 mg twice daily to about 50 mg twice daily. In some other embodiments, the suitable dosages are from about 30 mg twice daily to about 40 mg twice daily. In some other embodiments, the suitable dosages are from about 40 mg twice daily to about 50 mg twice daily. In other embodiments, suitable dosages are about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg per day, about 95 mg per day, about 100 mg per day, about 105 mg per day, about 110 mg per day, about 115 mg per day, or about 120 mg per day. In certain other embodiments, suitable dosages are about 10 mg, about 15 mg, about 20 mg, about 25 mg, about 30 mg, about 35 mg, about 40 mg, about 45 mg, about 50 mg, about 55 mg, or about 60 mg twice daily.

It will be understood that a suitable dosage of a selective inhibitor of Aurora A kinase may be taken at any time of the day or night. In some embodiments, a suitable dosage of a selective inhibitor of Aurora A kinase is taken in the morning. In some other embodiments, a suitable dosage of a selective inhibitor of Aurora A kinase is taken in the evening. In some other embodiments, a suitable dosage of a selective inhibitor of Aurora A kinase is taken both in the morning and the evening. It will be understood that a suitable dosage of a selective inhibitor of Aurora A kinase may be taken with or without food. In some embodiments a suitable dosage of a selective inhibitor of Aurora A kinase is taken with a meal. In some embodiments a suitable dosage of a selective inhibitor of Aurora A kinase is taken while fasting.

Suitable weekly dosages of paclitaxel can generally range, in single or divided or multiple doses, from about 40 mg/m$^2$ to about 80 mg/m$^2$ per week. Other suitable weekly dosages of paclitaxel can generally range, in single or divided or multiple doses, from about 50 mg/m$^2$ to about 75 mg/m$^2$ per week. Other suitable weekly dosages of paclitaxel can generally range, in single or divided or multiple doses, from about 60 mg/m$^2$ to about 70 mg/m$^2$ per week. In other embodiments, suitable weekly dosages are about 40 mg/m$^2$, about 45 mg/m$^2$, about 50 mg/m$^2$, about 55 mg/m$^2$, about 60 mg/m$^2$, about 65 mg/m$^2$, about 70 mg/m$^2$, or about 75 mg/m$^2$ per week.

Additionally, it will be appreciated that the frequency with which any of these therapeutic agents can be administered can be once or more than once over a period of about 2 days, about 3 days, about 4 days, about 5 days, about 6 days, about 7 days, about 8 days, about 9 days, about 10 days, about 20 days, about 28 days, about a week, about 2 weeks, about 3 weeks, about 4 weeks, about a month, about every 2 months, about every 3 months, about every 4 months, about every 5 months, about every 6 months, about every 7 months, about every 8 months, about every 9 months, about every 10 months, about every 11 months, about every year, about every 2 years, about every 3 years, about every 4 years, or about every 5 years.

For example, an agent may be administered daily, weekly, biweekly, or monthly for a particular period of time. In some embodiments, a certain amount of the selective Aurora A kinase inhibitor can be administered on a daily basis over a period of three days. Alternatively, an agent may be administered daily, weekly, biweekly, or monthly for a particular period of time followed by a particular period of non-treatment. In some embodiments, a certain amount of the selective Aurora A kinase inhibitor can be administered daily for three days followed by four days of no administration, followed by administration daily for three days followed by four more days of no administration, followed by administration daily for three days followed by four more days of no administration. In some embodiments, a certain amount of a taxane can be administered weekly over a three week period.

In some embodiments, the selective Aurora A kinase inhibitor and the taxane are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment.

In some embodiments, the treatment period during which an agent is administered is then followed by a non-treatment period of a particular time duration, during which the therapeutic agents are not administered to the patient. This non-treatment period can then be followed by a series of subsequent treatment and non-treatment periods of the same or different frequencies for the same or different lengths of time. In some embodiments, the treatment and non-treatment periods are alternated. It will be understood that the period of treatment in cycling therapy may continue until the patient has achieved a complete response or a partial response, at which point the treatment may be stopped. Alternatively, the period of treatment in cycling therapy may continue until the patient has achieved a complete response or a partial response, at which point the period of treatment may continue for a particular number of cycles. In some embodiments, the length of the period of treatment may be a particular number of cycles, regardless of patient response. In some other embodiments, the length of the period of treatment may continue until the patient relapses.

For example, a certain amount of the selective Aurora A kinase inhibitor can be administered twice daily for 3 days followed by 11 days of non-treatment followed by 3 days of twice daily administration. In some embodiments, the treatment and non-treatment periods are alternated. In other embodiments, a first treatment period in which a first amount of the selective inhibitor of Aurora A kinase is administered can be followed by another treatment period in which a same or different amount of the same or a different selective inhibitor of Aurora A kinase is administered. The second treatment period can be followed by other treatment periods. During the treatment and non-treatment periods, one or more additional therapeutic agents can be administered to the patient.

In one embodiment, the administration is on a 28-day dose schedule in which the selective Aurora A kinase inhibitor is administered twice-daily in a schedule of 3 days on followed by 4 days off, repeated weekly for three weeks concomitantly with the first dose of once-weekly paclitaxel, repeated weekly for 3 weeks (the twice-daily selective Aurora A kinase inhibitor is given on days 1, 2, 3, 8, 9, 10, 15, 16, and 17; and the weekly paclitaxel is given on days 1, 8, and 15 of the 28-day schedule). In some embodiments, the dose schedules for the selective Aurora A kinase inhibitors described herein are dose schedules for administration of alisertib.

In another embodiment, the administration is on a 28-day dose schedule in which the selective Aurora A kinase inhibitor is administered twice-daily in a schedule of 2 days on followed by 5 days off, repeated weekly for three weeks concomitantly with the first dose of once-weekly paclitaxel, repeated weekly for 3 weeks (the twice-daily selective Aurora A kinase inhibitor is given on days 1, 2, 8, 9, 15, and 16; and the weekly paclitaxel is given on days 1, 8, and 15 of the 28-day schedule). In some embodiments, the dose schedules for the selective Aurora A kinase inhibitors described herein are dose schedules for administration of alisertib.

In one embodiment, the administration is on a 28-day dose schedule in which the selective Aurora A kinase inhibitor is administered twice-daily in a schedule of 3 days on followed by 4 days off, repeated weekly for two weeks concomitantly with the first dose of once-weekly paclitaxel, repeated weekly for 3 weeks (the twice-daily selective Aurora A kinase inhibitor is given on days 1, 2, 3, 8, 9, and 10; and the weekly paclitaxel is given on days 1, 8, and 15 of the 28-day schedule). In some embodiments, the dose schedules for the selective Aurora A kinase inhibitors described herein are dose schedules for administration of alisertib.

In another embodiment, the administration is on a 28-day dose schedule in which the selective Aurora A kinase inhibitor is administered twice-daily in a schedule of 3 days on followed by 11 days off, repeated once, concomitantly with the first and third dose of once-weekly paclitaxel, repeated weekly for 3 weeks (the twice-daily selective Aurora A kinase inhibitor is given on days 1, 2, 3, 15, 16, and 17; and the weekly paclitaxel is given on days 1, 8, and 15 of the 28-day schedule). In some embodiments, the dose schedules for the selective Aurora A kinase inhibitors described herein are dose schedules for administration of alisertib.

The selective inhibitor of Aurora A kinase can be administered by any method known to one skilled in the art. For example, the selective inhibitor of Aurora A kinase can be administered in the form of a composition, in one embodiment a pharmaceutical composition of the selective inhibitor of Aurora A kinase and a pharmaceutically acceptable carrier, such as those described herein. Preferably, the pharmaceutical composition is suitable for oral administration. In some embodiments, the pharmaceutical composition is a tablet for oral administration, such as an enteric coated tablet. Such tablets are described in US Publication No. 2010/0310651, which is hereby incorporated by reference in its entirety. In some other embodiments, the pharmaceutical composition is a liquid dosage form for oral administration. Such liquid dosage forms are described in US Publication No. 2011/0039826, hereby incorporated by reference. In certain embodiments, these compositions optionally further comprise one or more additional therapeutic agents.

The taxane (e.g., paclitaxel or docetaxel) can be administered by any method known to one skilled in the art. For example, the taxane can be administered in the form of a composition, in one embodiment a pharmaceutical composition of a taxane and a pharmaceutically acceptable carrier, such as those described herein. In some embodiments, the pharmaceutical composition is a liquid dosage form, which can be administered via an intravenous route, such as intravenous injection or intravenous infusion. In one embodiment, paclitaxel is administered via intravenous injection. In another embodiment ABRAXANE® is administered via intravenous injection. Such pharmaceutical compositions are described in U.S. Pat. No. 6,096,331 and U.S. Pat. No. 6,506,405.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The terms "carrier", "adjuvant", or "vehicle" are used interchangeably herein, and include any and all solvents, diluents, and other liquid vehicles, dispersion or suspension aids, surface active agents, isotonic agents, thickening or emulsifying agents, preservatives, solid binders, lubricants and the like, as suited to the particular dosage form desired. *Remington: The Science and Practice of Pharmacy.* 20th Ed., ed. A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as disodium hydrogen phosphate, potassium hydrogen phosphate, sodium carbonate, sodium bicarbonate, potassium carbonate, potassium bicarbonate, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compositions for use in the method of the invention may be formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present invention will be decided by the attending physician within the scope of sound medical judgment. A unit dosage form for parenteral administration may be in ampoules or in multi-dose containers.

The present invention is also directed to kits and other articles of manufacture for treating proliferative diseases. In one embodiment, a kit is provided that comprises a selective inhibitor of Aurora A kinase, or a pharmaceutically acceptable salt thereof, as described herein; a taxane, or a pharmaceutically acceptable salt thereof, as described herein; and instructions. The kit may optionally further include the one or more additional therapeutic agents, as described herein. The instructions may indicate the disease state for which the kit is to be used, storage information, dosing information and/or instructions regarding how to administer the selective inhibitor of Aurora A kinase, the taxane, and/or additional therapeutic agent or agents. The kit may also comprise packaging materials. The packaging material may comprise a container for housing the contents of the kit. The kit may also optionally comprise additional components, such as syringes for administration of the contents of the kit. The kit may comprise the selective inhibitor Aurora A kinase, the taxane, and/or additional therapeutic agent or agents in single or multiple dose forms.

In another embodiment, an article of manufacture is provided that comprises the selective inhibitor of Aurora A kinase, or a pharmaceutically acceptable salt thereof; taxane, or a pharmaceutically acceptable salt thereof; and packaging materials. The article of manufacture may optionally further include the one or more additional therapeutic agents. The packaging material may comprise a container for housing the contents of the article of manufacture. The container may optionally comprise a label indicating the disease state for which the article is to be used, storage information, dosing information and/or instructions regarding how to administer the selective inhibitor of Aurora A kinase, taxane, and/or additional therapeutic agent or agents. The article may also optionally comprise additional components, such as syringes for administration of the composition. The article may comprise the selective inhibitor of Aurora A kinase, taxane, and/or additional therapeutic agent or agents in single or multiple dose forms.

A wide variety of therapeutic agents may have a therapeutically relevant added benefit in combination with the combination of a selective inhibitor of Aurora A kinase and a taxane of the present invention. Combination therapies that comprise the combination of a selective inhibitor of Aurora A kinase and a taxane of the present invention with one or more other therapeutic agents can be used, for example, to: 1) enhance the therapeutic effect(s) of the methods of the present invention and/or the one or more other therapeutic agents; 2) reduce the side effects exhibited by the methods of the present invention and/or the one or more other therapeutic agents; and/or 3) reduce the effective dose of the selective inhibitor of Aurora A kinase and the taxane of the present invention and/or the one or more other therapeutic agents.

In some embodiments, the method of the invention comprises administration of a selective inhibitor of Aurora A kinase in combination with a taxane and an additional therapeutic agent, wherein the amounts of each agent are therapeutically effective when used in combination.

In certain embodiments, the selective inhibitor of Aurora A kinase in combination with a taxane is administered with the concomitant or sequential administration of cisplatin or doxorubicin. It will be appreciated that combination therapy includes administration of the therapeutic agents concurrently or sequentially. Alternatively, the therapeutic agents can be combined into one composition which is administered to the patient.

Examples of therapeutic agents that may be used in combination with the combination of a selective inhibitor of Aurora A kinase and a taxane of the present invention include, but are not limited to, anti-proliferative agents, anticancer agents, alkylating agents, antibiotic agents, antimetabolic agents, hormonal agents, plant-derived agents, and biologic agents. Examples of some of the above classes of additional therapeutic agents are listed below for purposes of illustration and not for purposes of limitation, as these examples are not all-inclusive. Many of the examples below could be listed in multiple classes of anti-cancer agents and are not restricted in any way to the class in which they are listed.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including an inhibitor of the present invention and an alkylating agent may have therapeutic synergistic effects on cancer and reduce sides affects associated with these chemotherapeutic agents.

Antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including an inhibitor of the present invention and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including an inhibitor of the present invention and a antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, and flutamide), aromatase inhibitors (e.g., aminoglutethimide, anastrozole and tetrazole), ketoconazole, goserelin acetate, leuprolide, megestrol acetate and mifepristone. Combination therapy including an inhibitor of the present invention and a hormonal agent may have therapeutic synergistic effects on cancer and reduce sides effects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), and podophyllotoxins (e.g., etoposide (VP-16) and teniposide (VM-26)). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including an inhibitor of the present invention and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including an inhibitor of the present invention and a biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with inhibitors of the present invention include, but are not limited to, interleukin 2 (IL-2), and interleukin 4 (IL-4), interleukin 12 (IL-12).

Interferons include more than 23 related subtypes with overlapping activities, all of the IFN subtypes within the scope of the present invention. IFN has demonstrated activity against many solid and hematologic malignancies, the later appearing to be particularly sensitive.

Other cytokines that may be used in conjunction with the inhibitors of the present invention include those cytokines that exert profound effects on hematopoiesis and immune functions. Examples of such cytokines include, but are not limited to erythropoietin, granulocyte-CSF (filgrastin), and granulocyte, macrophage-CSF (sargramostim). These cytokines may be used in conjunction with an inhibitor of the present invention to reduce chemotherapy-induced myelopoietic toxicity.

Other immuno-modulating agents other than cytokines may also be used in conjunction with the inhibitors of the present invention to inhibit abnormal cell growth. Examples of such immuno-modulating agents include, but are not limited to bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein.

Combination therapy including an inhibitor of the present invention and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant CD20$^+$ pre-B and mature B cells. RITUXAN® is used as single agent for the treatment of patients with relapsed or refractory low-grade or follicular, CD20+, B cell non-Hodgkin's lymphoma. Combination therapy including an inhibitor of the present invention and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WTI, BRCA1, and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WTI is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including an inhibitor of the present invention and a tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), alpha-fetoprotein (AFP), carcinoembryonic antigen (CEA) (produced by colon cancers and other adenocarcinomas, e.g. breast, lung, gastric, and pancreas cancer s), melanoma associated antigens (MART-1, gp 100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

In certain embodiments, the one or more additional treatments is selected from radiation, chemotherapy, immunotherapy, or other targeted anticancer therapy.

Cancers to be Treated with the Selective Inhibitor of Aurora A kinase or Combinations Thereof The present invention provides new methods for the treatment of cell proliferative disorders. As used herein, the term "cell proliferative disorders" includes, but is not limited to, cancerous hyperproliferative disorders (e.g., brain, lung, squamous cell, bladder, gastric, pancreatic, breast, head, neck, renal, liver, kidney, ovarian, prostate, colorectal, colon, epidermoid, esophageal, testicular, gynecological or thyroid cancer, acute myeloid leukemia, multiple myeloma, mesothelioma, Non-small cell lung carcinoma (NSCLC), small cell lung cancer (SCLC), neuroblastoma, and acute lymphoblastic leukemia (ALL)); non-cancerous hyperproliferative disorders (e.g., benign hyperplasia of the skin (e.g., psoriasis), restenosis, and benign prostatic hypertrophy (BPH)); and diseases related to vasculogenesis or angiogenesis (e.g., tumor angiogenesis, hemangioma, glioma, melanoma, Kaposi's sarcoma and ovarian, breast, lung, pancreatic, prostate, colon and epidermoid cancer). Cell proliferative disorders further encompass primary and metastatic cancers.

In particular, the compounds are useful in the treatment of cancers in a subject, including, but not limited to, lung and bronchus, including non-small cell lung cancer (NSCLC), squamous lung cancer, brochioloalveolar carcinoma (BAC), adenocarcinoma of the lung, and small cell lung cancer (SCLC); prostate, including androgen-dependent and androgen-independent prostate cancer, breast, including metastatic breast cancer, pancreas; colon and rectum; thyroid; liver and intrahepatic bile duct; hepatocellular; gastric; endometrial; melanoma; kidney; and renal pelvis, urinary bladder; uterine corpus; uterine cervix; ovary, including progressive epithelial or primary peritoneal cancer, multiple myeloma; esophagus; acute myelogenous leukemia (AML); chronic myelogenous leukemia (CML), including accelerated CML and CML blast phase (CML-BP); lymphocytic leukemia; myeloid leukemia; acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma, including diffuse large B-cell lymphoma (DLBCL); T-cell lymphoma; multiple myeloma (MM); amyloidosis; Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes; brain, including glioma/glioblastoma, anaplastic oligodendroglioma, and adult anaplastic astrocytoma; neuroendocrine, including metastatic neuroendocrine tumors; head and neck, including, e.g., squamous cell carcinoma of the head and neck, and nasopharyngeal cancer, oral cavity; and pharynx; small intestine; bone; soft tissue sarcoma; and villous colon adenoma.

In one embodiment, diseases or disorders treatable by the combination of Aurora A kinase selective inhibitors and taxanes, include, but are not limited to, ovarian cancer, breast cancer, prostate cancer, gastric cancer, head and neck cancer, bladder cancer, lung cancer, epithelial ovarian cancer, fallopian tube cancer, primary peritoneal cancer, and AIDS-related Kaposi's sarcoma. In another embodiment, diseases or disorders treatable by the combination of Aurora A kinase selective inhibitors and taxanes, include, but are not limited to, ovarian cancer, breast cancer, lung cancer, and AIDS-related Kaposi's sarcoma. In yet another embodiment, the disease or disorder treatable by the combination of Aurora A kinase selective inhibitors and taxanes is ovarian cancer, epithelial ovarian cancer, fallopian tube cancer, or primary peritoneal cancer. In another embodiment, diseases or disorders treatable by the combination of Aurora A kinase selective inhibitors and taxanes, include, but are not limited to, small cell lung cancer.

Determining the Effect of the Selective Inhibitor of Aurora A kinase in combination with Paclitaxel:

Preferably, the method according to the invention causes an inhibition of cell proliferation of the contacted cells. The phrase "inhibiting cell proliferation" is used to denote an ability of a selective inhibitor of Aurora A kinase and/or taxane to inhibit cell number or cell growth in contacted cells as compared to cells not contacted with the inhibitors. An assessment of cell proliferation can be made by counting cells using a cell counter or by an assay of cell viability, e.g., a BrdU, MIT, XTT, or WST assay, and comparing the size of the growth of contacted cells with non-contacted cells. Where the cells are in a solid growth (e.g., a solid tumor or organ), such an assessment of cell proliferation can be made by measuring the growth, e.g., with calipers or non-invasive imaging such as MRI and PET.

Preferably, the growth of cells contacted with a selective inhibitor of Aurora A kinase and a taxane is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, a selective inhibitor of Aurora A kinase and/or a taxane that inhibits cell proliferation in a contacted cell may induce the contacted cell to undergo growth retardation, to undergo growth arrest, to undergo programmed cell death (i.e., apoptosis), or to undergo necrotic cell death.

4. Experimental Procedures

In the Examples described below, alisertib (MLN8237) refers to the sodium salt, sodium 4-{[9-chloro-7-(2-fluoro-6-methoxyphenyl)-5H-pyrimido[5,4-d][2]benzazepin-2-yl]amino}-2-methoxybenzoate monohydrate.

EXAMPLE 1

In Vivo Efficacy Studies of Alisertib Administration in Combination with Paclitaxel Administration in a Breast Cancer Mouse Model Experimental Procedure Tumor cell culture and primary human tumors. MDA-MB-231 cells were obtained from ATCC and cultured in DMEM medium supplemented with heat inactivated 10% FBS and 1% L-glutamine. MDA-MB-231 cells ($2 \times 10^{\wedge}2$) were injected orthotopically into the mammary fat pad of nude mice. In vivo efficacy studies. Nude mice bearing xenograft tumors (MDA-MB-231); (n=10 animals/group) were dosed orally (PO) with vehicle or alisertib (10, 20 mg/kg) for 21 days using a once daily schedule (QD). Paclitaxel (5, 10, 20 and 30 mg/kg) was administered intravenously (IV) on a once weekly schedule (QW) for a total of three doses. Tumor growth was measured using vernier calipers and tumor growth inhibition (TGI) was calculated using the following formula: TGI=(Δcontrol−Δtreated)*100/Δcontrol. Tumor Growth Delay (TGD) is the time (days) for each treatment group to reach an average tumor volume of 1000 mm$^3$ relative to the vehicle treated group. Statistical significance in the tumor growth between pairs of treatment groups were assessed using linear mixed effects regression models. These models account for the fact that each animal was measured at multiple time points. A separate model was fit for each comparison, and the areas under the curve (AUC) for each treatment group were calculated using the predicted values from the model. The percent decrease in AUC (dAUC) relative to the reference group was then calculated.

Results

Table 1 illustrates that alisertib demonstrated additive and synergistic antitumor activity in combination with paclitaxel in an orthotopic breast cancer in vivo xenograft model. Moreover, significant tumor growth delay occurred relative to the single agents after discontinuing treatment.

TABLE 1

| Model[a] | MLN8237 dose (QD) | Paclitaxel dose (Q7D × 3) | TGI[b] (%) | Days to 1000 mm$^3$ | Outcome (AUC)[c] |
|---|---|---|---|---|---|
| MDA-MB-231 | 20 mg/kg | 30 mg/kg | 101.4 | 35 | Synergistic |
| | 20 mg/kg | 20 mg/kg | 95.3[d] | 24.8[d] | Synergistic |
| | 20 mg/kg | 15 mg/kg | 85.7 | 15.7 | Additive |
| | 20 mg/kg | 10 mg/kg | 45.87 | 4.2 | Additive |
| | 20 mg/kg | 5 mg/kg | 43.6 | 4 | Additive |
| | 10 mg/kg | 30 mg/kg | 102.4 | 31.2 | Synergistic |
| | 10 mg/kg | 20 mg/kg | 81.9 | 13.4 | Additive |
| | 10 mg/kg | 15 mg/kg | 85.6 | 13.7 | Additive |
| | 10 mg/kg | 10 mg/kg | 42.3 | 4.2 | Additive |
| | 3 mg/kg | 20 mg/kg | 64.9[d] | 8.8[d] | Additive |
| | 3 mg/kg | 10 mg/kg | 21.7 | 1.9 | Additive |
| | 3 mg/kg | 5 mg/kg | 20.8 | 2 | Additive |

[a]Orthotopic breast cancer models were grown in nude mice and treated daily with alisertib administered orally for 21 days with paclitaxel dosed IV once per week
[b]Tumor growth inhibition (TGI) = (Δ treated/Δ control) × 100/Δ control, was calculated on the last day of treatment
[c]Synergy analysis based on the area under the curve (AUC) values days 0 through 20
[d]Average of 2 studies Statistical Analysis for In Vivo Data For the MDA-MB-231 model, measurements from day 0 to 20 were analyzed. All tumor volumes had a value of 1 added to them before $\log_{10}$ transformation. These values were compared across treatment groups to assess whether the differences in the trends over time were statistically significant. To compare pairs of treatment groups, the following mixed-effects linear regression model was fit to the data using the maximum likelihood method:

$$Y_{ijk} - Y_{i0k} = Y_{i0k} + treat_i + day_j + day_j^2 + (treat*day)_{ij} + (treat*day^2)_{ij} + e_{ijk}$$

where $Y_{ijk}$ is the $\log_{10}$ tumor value at the $j^{th}$ time point of the $k^{th}$ animal in the $i^{th}$ treatment, $Y_{i0k}$ is the day 0 $\log_{10}$ tumor value in the $k^{th}$ animal in the $i^{th}$ treatment, $day_j$ was the median-centered time point and was treated as a continuous variable, and $e_{ijk}$ is the residual error. A spatial power law covariance matrix was used to account for the repeated measurements on the same animal over time. Interaction terms as well as $day_j^2$ terms were removed if they were not statistically significant.

A likelihood ratio test was used to assess whether a given pair of treatment groups exhibited differences which were statistically significant. The −2 log likelihood of the full model was compared to one without any treatment terms (reduced model) and the difference in the values was tested using a Chi-squared test. The degrees of freedom of the test were calculated as the difference between the degrees of freedom of the full model and that of the reduced model.

In addition to the statistical significance, a measure of the magnitude of the effect for each treatment was found. The predicted differences in the log tumor values ($Y_{ijk}-Y_{i0k}$) vs. time were taken from the above model to calculate mean area under the curve (AUC) values for each treatment group. A dAUC value was then calculated as:

$$dAUC = 100 \frac{\text{mean}(AUC_{control}) - \text{mean}(AUC_{treatment})}{|\text{mean}(AUC_{control})|}$$

For synergy analyses, the observed differences in the log tumor values were used to calculate AUC values for each animal. In instances when an animal in a treatment group was removed from the study, the last observed tumor value was carried forward through all subsequent time points. The synergy score for the combination of treatments A and B was defined as 100*(mean($AUC_{AB}$)−mean($AUC_A$)−mean($AUC_B$)+mean($AUC_{ctl}$))/mean($AUC_{ctl}$)

where $AUC_{AB}$, $AUC_A$, $AUC_B$, and $AUC_{ctl}$ are the AUC values for animals in the combination group, the A group, the B group, and the control group, respectively. The standard error of the synergy score was computed based on the variation in the AUC values among the animals. A two sided t-test was used to determine if the synergy score was significantly different from zero. If the P-value was below 0.05, and the synergy score was less than zero, then the combination was considered to be synergistic. If the P-value was above 0.05, then the combination was considered to be additive.

EXAMPLE 2

Semi-Mechanistic Neutropenia Model

As neutropenia is a common dose-limiting toxicity for taxanes and alisertib, a semi-mechanistic model was developed to predict the time course of plasma PK versus absolute neutrophil count (ANC) to aid in dose and schedule selection for the combination of alisertib and paclitaxel. This model accounts for the time delay between agent exposure and ANC since the agents affect the progenitor cells rather than the neutrophils directly.

The model was used to describe neutropenia using PK and ANC data from mice or rats dosed over multiple days with alisertib and/or taxane treatment. To construct the model, rodents were administered docetaxel and alisertib, or the combination of the two, and ANC was quantified predose and on scheduled days dependent on administration schedule. Rats received docetaxel (3.5 to 10 mg/kg IV on Day 1) and alisertib (5 to 35 mg/kg PO QDx3, 7, or 14) or the combination of the two. ANC was quantified predose and on Days 1, 2, 4, 6, 8, 11, 14, and 17.

A compartmental PK model was used to describe time dependent drug concentrations and neutropenia was described using a semi-mechanistic model as described by Friberg et al. (Friberg et al J Clin Oncol. 2002; 20(24):4713-21). Alisertib human PK values were projected from chimpanzee PK values and human systems and taxane drug-related parameters were obtained from published sources and in vitro data from rodent and human CFU-GM cell lines. Differences in plasma protein binding and CFU-GM IC50s were used to correct for human-rodent interspecies variation. The model was extended from docetaxel to paclitaxel by replacing the drug related parameters (PK and Slope) with published values for paclitaxel.

This preclinical model predicted that decreasing the weekly paclitaxel dose would allow achievement of higher tolerable alisertib doses. This prediction was confirmed in the dose escalation study, described in Example 3, below. The model also predicted that skipping the second week of alisertib dosing would further mitigate neutropenia, allowing for additional alisertib dose escalation or dose modification in patients that suffer mechanistic toxicities after cycle 1.

EXAMPLE 3

Dose Escalation Study

Table 2 describes clinical evaluation of the safety and antitumor activity of alisertib and paclitaxel in recurrent ovarian cancer patients. In this clinical study, alisertib was dosed BID 3 days on/4 days off concomitantly with the first dose of QWx3 paclitaxel on a 28-day schedule. It was determined that with paclitaxel dosed weekly at 80 mg/m$^2$, 10 mg BID of alisertib was tolerated (e.g. considered to be a safe dose) whereas with paclitaxel dosed weekly at 60 mg/m$^2$, 40 mg BID of alisertib was tolerated.

TABLE 2

| Dosage of paclitaxel | Dosage of alisertib | Clinical Observation |
| --- | --- | --- |
| 80 mg/m$^2$ weekly | 10 mg BID | No dose limiting toxicities |
| 80 mg/m$^2$ weekly | 20 mg BID | 2 of 6 patients with dose limiting toxicities[a] |
| 60 mg/m$^2$ weekly | 20 mg BID | No dose limiting toxicities |
| 60 mg/m$^2$ weekly | 30 mg BID | 1 of 6 patients with dose limiting toxicities[b] |
| 60 mg/m$^2$ weekly | 40 mg BID | No dose limiting toxicities |
| 60 mg/m$^2$ weekly | 50 mg BID | 3 of 3 patients with dose limiting toxicities[c] |

[a]Dose limiting toxicities include gastrointestinal toxicities (diarrhea, nausea, vomiting) and oral mucositis
[b]Dose limiting toxicities include neutropenia coincident fever.
[c]Dose limiting toxicities include drowsiness/confusion, neutropenia, and oral mucositis.

EXAMPLE 4

Exposure-Efficacy Model

An exposure-efficacy model was developed to predict which combination of alisertib and paclitaxel results in the greatest antitumor efficacy. Isobolograms comparing alisertib and paclitaxel exposures to tumor growth inhibition were generated from in vivo efficacy studies in tumor-bearing mice, as described in Example 1. The clinically achieved exposures of alisertib and paclitaxel from the dose escalation study, described in Example 3, were mapped onto the isobologram by correcting for mice-human variation in plasma protein binding and maximum tolerated exposures for both agents. These data demonstrate that 80 and 60 mg/m$^2$ paclitaxel will lead to similar levels of efficacy, consistent with clinical observations in some cancer indications. The higher alisertib doses (40 mg BID) attained with 60 mg/m$^2$ paclitaxel in the dose escalation study are predicted to lead to greater efficacy than 10 mg BID alisertib with 80 mg/m$^2$ paclitaxel.

EXAMPLE 5

In Vivo Tumor Models of Small Cell Lung Cancer

The antitumor activity of alisertib was tested in combination with paclitaxel in multiple models of human SCLC when grown in immunocompromised mice. The data presented here demonstrate added antitumor benefit of alisertib combined with paclitaxel in SCLC xenograft models.

NCI-H69.

Procedure. NCI-H69 is an established small cell lung cancer cell line. See, e.g., A. W. Tong et al., Cancer Res. 1984 November; 44(11):4987-92. Treatments began when tumors reached approximately 200 mm$^3$ following subcutaneous tumor implantation with NCI-H69 tumor fragments for all groups containing 10 female immunocompromised nu/nu mice per group. MLN8237 was tested at a dose of 20 mg/kg administered PO on a QIDx21-Q8Hx2 schedule and at doses of 20 and 10 mg/kg on a QIDx21 schedule. Paclitaxel was tested at doses of 30 and 15 mg/kg administered IV on a Q7Dx3 schedule. Each paclitaxel dose was combined with each MLN8237 dose on the QDx21 treatment schedule. In the combination treatment groups MLN8237 was administered first to the animals, followed immediately by the administration of paclitaxel. One group served as a vehicle-treated control group receiving PO treatment with the MLN8237 vehicle on a QIDx21 schedule.

Summary. In the SCLC cell line xenograft NCI-H69, alisertib at 10 mg/kg QD and paclitaxel at 15 mg/kg twice weekly (QW) led to marked increase in antitumor activity, and alisertib at 20 mg/kg QD with paclitaxel at 15 mg/kg QW led to sustained cures even after terminating treatment. See FIG. 1 (BID=twice daily; IV=intravenous; MLN8237=alisertib; PO=oral; QD=once daily. Tumor bearing mice were treated for 21 days with alisertib (PO, QD, or BID), paclitaxel (IV, QW), or the combination of both at the indicated doses. Tumors were measured twice weekly. Bars represent standard error of the mean. The shaded areas indicate the 21 day treatment period.). In this model, alisertib and paclitaxel at their single agent maximum tolerated doses in mice of 20 mg/kg BID and 30 mg/kg QD led to prolonged regressions and sustained cures respectively.

NCI-H82.

Procedure. NCI-H82 is an established small cell lung cancer cell lines. See, e.g., Y. Nakanishi et al., Exp Cell Biol. 1988; 56(1-2):74-85. Treatments began when tumors reached approximately 200 mm$^3$ following subcutaneous tumor implantation with NCI-H82 tumor fragments for all groups containing 10 female immunocompromised nu/nu mice per group. MLN8237 was tested at a dose of 20 mg/kg administered PO on a QIDx21-Q8Hx2 schedule and at doses of 20 and 10 mg/kg on a QIDx21 schedule. Paclitaxel was tested at doses of 30 and 15 mg/kg administered IV on a Q7Dx3 schedule. Each paclitaxel dose was combined with each MLN8237 dose on the QDx21 treatment schedule. In the combination treatment groups MLN8237 was administered first to the animals, followed immediately by the administration of paclitaxel. One group served as a vehicle-treated control group receiving PO treatment with the MLN8237 vehicle on a QIDx21 schedule.

Figure 2:
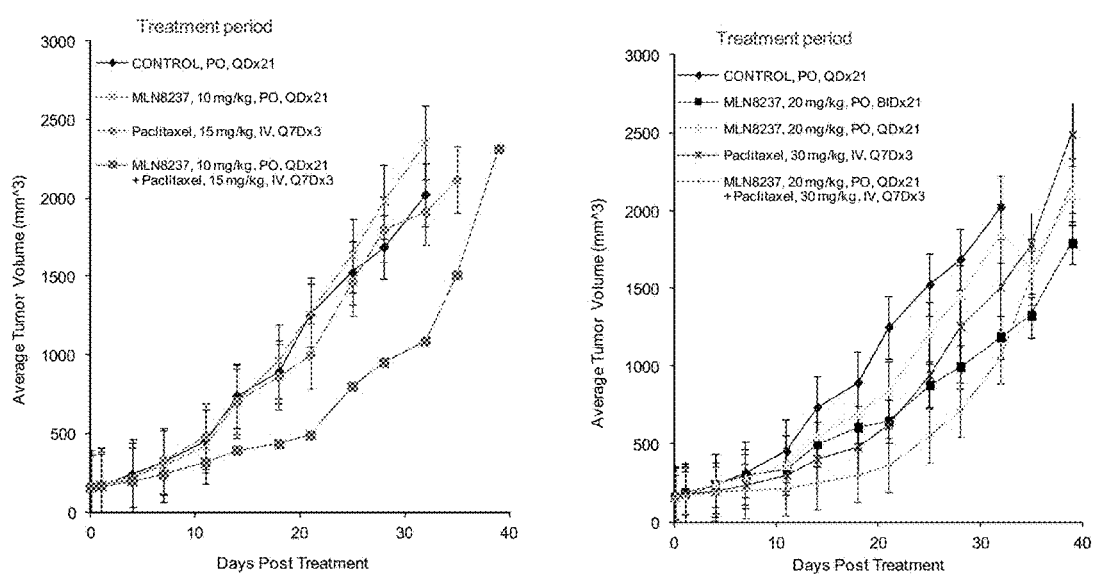
FIG. 2 shows the antitumor activity (average tumor volume as a function of time) of alisertib combined with paclitaxel in the NCI-H82 small cell lung cancer tumor model.

Summary. The antitumor activity of alisertib in combination with paclitaxel was tested in the SCLC cell line xenograft NCI-H82. Alisertib at 10 mg/kg QD and paclitaxel at 15 mg/kg QW as single agents had no antitumor activity, but in combination led to increased antitumor activity relative to the single agents. See FIG. 2 (BID=twice daily; IV=intravenous; MLN8237=alisertib; PO=oral; QD=once daily. Tumor bearing mice were treated for 21 days with alisertib (PO, QD, or BID), paclitaxel (IV, QW), or the combination of both at the indicated doses. Tumors were measured twice weekly. Bars represent standard error of the mean. The shaded areas indicate the 21 day treatment period.). A moderate increase in antitumor activity also occurred with alisertib at 20 mg/kg QD and paclitaxel at 30 mg/kg QW relative to the single agents and relative to the alisertib single agent maximum tolerated dose of 20 mg/kg BID.

CTG-0166.

Procedure. CTG-0166 is a small cell lung cancer cell line (Champions Oncology, Baltimore, Md., www.championsoncology.com). Treatments began when tumors reached between 180 and 250 mm$^3$ following subcutaneous tumor implantation with CTG-0166 tumor fragments for all groups containing 8 female immunocompromised nu/nu mice per group. MLN8237 was tested at a dose of 20 mg/kg on a QIDx21 schedule administered PO, paclitaxel was tested at a dose of 15 mg/kg on a Q7Dx3 schedule administered IV and topotecan was tested at a dose of 1.5 mg/kg on a QDx5 schedule administered IV. In the combination treatment groups MLN8237 was administered first to the animals, followed immediately by the administration of paclitaxel. One group served as a vehicle-treated control group receiving PO treatment with the MLN8237 vehicle on a QIDx21 schedule.

Figure 3:
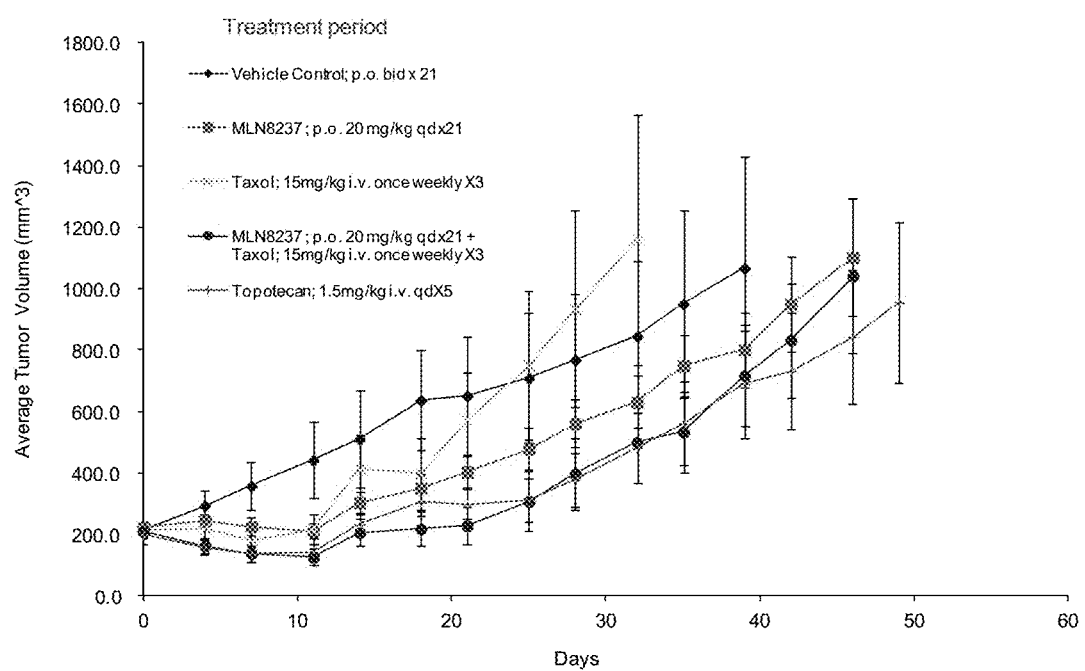
FIG. 3 shows the antitumor activity (average tumor volume as a function of time) of alisertib combined with paclitaxel in the CTG-0166 primary small cell lung cancer tumor model.

Summary. In human primary SCLC model CTG-0166, the combination of alisertib at 20 mg/kg QD and paclitaxel at 15 mg/kg QW led to a slight increase in antitumor activity relative to the respective single doses. See FIG. 3 (BID=twice daily; IV=intravenous; MLN8237=alisertib; PO=oral; QD=once daily. Tumor bearing mice were treated for 21 days with alisertib (PO, QD), paclitaxel (IV, QW), or the combination of both at the indicated doses. Topotecan (IV, Q5D) was included as a control. Tumors were measured twice weekly. Bars represent standard error of the mean. The shaded areas indicate the 21 day treatment period.). In this model, topotecan at its single agent maximum tolerated dose of 1.5 mg/kg Q5D was also tested.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are herein described. All publications mentioned herein are hereby incorporated by reference in their entirety for the purpose of describing and disclosing the materials and methodologies that are reported in the publication which might be used in connection with the invention.

What is claimed is:

1. A method of treating small-cell lung cancer in a subject in need thereof, consisting of administering to the subject on a 28-day dose schedule a twice-daily dose of an Aurora A kinase inhibitor, wherein the Aurora A kinase inhibitor is 4-{[9-chloro-7-(2-fluoro-6-methoxyphenyl)-5H-pyrimido [5,4-d][2]benzazepin-2-yl]amino}-2-m ethoxybenzoic acid, or a pharmaceutically acceptable salt thereof, in combination with a once-weekly dose of paclitaxel, wherein the administered twice-daily dose of the Aurora A kinase inhibitor is about 30 mg, about 35 mg, about 40 mg, or about 45 mg, and is administered on days 1-3, 8-10, and 15-17 of the 28-day schedule; and the administered once-weekly dose of paclitaxel is from about 40 mg/m$^2$ to about 80 mg/m$^2$, and is administered on days 1, 8, and 15 of the 28-day schedule.

2. The method of claim 1, wherein the administration of the Aurora A kinase inhibitor is concomitant with the administration of paclitaxel.

3. The method of claim 1, wherein the twice-daily dose of the Aurora A kinase inhibitor is about 30 mg.

4. The method of claim 1, wherein the twice-daily dose of the Aurora A kinase inhibitor is about 35 mg.

5. The method of claim 1, wherein the twice-daily dose of the Aurora A kinase inhibitor is about 40 mg.

6. The method of claim 1, wherein the twice-daily dose of the Aurora A kinase inhibitor is about 45 mg.

7. The method of claim 1, wherein the once-weekly dose of paclitaxel is from about 60 mg/m$^2$ to about 70 mg/m$^2$.

8. The method of claim 1, wherein the once-weekly dose of paclitaxel is about 60 mg/m$^2$.

9. The method of claim 1, wherein the Aurora A kinase inhibitor is sodium 4-{[9-chloro-7-(2-fluoro-6-methoxyphenyl)-5H-pyrimido[5,4-d][2]benzazepin-2-yl]amino}-2-methoxybenzoate.

10. The method of claim 2, wherein the Aurora A kinase inhibitor is sodium 4-{[9-chloro-7-(2-fluoro-6-methoxyphenyl)-5H-pyrimido[5,4-d][2]benzazepin-2-yl]amino}-2-methoxybenzoate.

11. The method of claim 3, wherein the Aurora A kinase inhibitor is sodium 4-{[9-chloro-7-(2-fluoro-6-methoxyphenyl)-5H-pyrimido[5,4-d][2]benzazepin-2-yl]amino}-2-methoxybenzoate.

12. The method of claim 4, wherein the Aurora A kinase inhibitor is sodium 4-{[9-chloro-7-(2-fluoro-6-methoxyphenyl)-5H-pyrimido[5,4-d][2]benzazepin-2-yl]amino}-2-methoxybenzoate.

13. The method of claim 5, wherein the Aurora A kinase inhibitor is sodium 4-{[9-chloro-7-(2-fluoro-6-methoxyphenyl)-5H-pyrimido[5,4-d][2]benzazepin-2-yl]amino}-2-methoxybenzoate.

14. The method of claim 6, wherein the Aurora A kinase inhibitor is sodium 4-{[9-chloro-7-(2-fluoro-6-methoxyphenyl)-5H-pyrimido[5,4-d][2]benzazepin-2-yl]amino}-2-methoxybenzoate.

15. The method of claim 7, wherein the Aurora A kinase inhibitor is sodium 4-{[9-chloro-7-(2-fluoro-6-methoxyphenyl)-5H-pyrimido[5,4-d][2]benzazepin-2-yl]amino}-2-methoxybenzoate.

16. The method of claim 8, wherein the Aurora A kinase inhibitor is sodium 4-{[9-chloro-7-(2-fluoro-6-methoxyphenyl)-5H-pyrimido[5,4-d][2]benzazepin-2-yl]amino}-2-methoxybenzoate.

\* \* \* \* \*